US010514379B2

(12) United States Patent
Hu et al.

(10) Patent No.: US 10,514,379 B2
(45) Date of Patent: Dec. 24, 2019

(54) DUAL RANGE CARDIAC TROPONIN IMMUNOASSAY DEVICES AND METHODS USING IMMUNOSENSOR AND MAGNETIC IMMUNOSENSOR

(71) Applicant: Abbott Point of Care Inc., Princeton, NJ (US)

(72) Inventors: Jing Hua Hu, Ottawa (CA); Antti Leo Oskari Virtanen, Ottawa (CA); Eric Edward Potter, Ottawa (CA); James T. K. Smith, North Grover (CA); Cary James Miller, Ottawa (CA); John Lewis Emerson Campbell, Ottawa (CA); Adam Roger Moss, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

(21) Appl. No.: 15/836,135

(22) Filed: Dec. 8, 2017

(65) Prior Publication Data
US 2018/0164306 A1   Jun. 14, 2018

Related U.S. Application Data

(60) Provisional application No. 62/432,297, filed on Dec. 9, 2016.

(51) Int. Cl.
*G01N 33/543* (2006.01)
*G01N 33/539* (2006.01)
(Continued)

(52) U.S. Cl.
CPC ..... *G01N 33/54333* (2013.01); *G01N 27/745* (2013.01); *G01N 33/539* (2013.01);
(Continued)

(58) Field of Classification Search
CPC ....... G01N 33/54333; G01N 33/54326; G01N 33/5438; G01N 33/6887; G01N 27/745; G01N 33/539; G01N 33/54353
See application file for complete search history.

(56) References Cited

U.S. PATENT DOCUMENTS

| 4,954,087 A | 9/1990 | Lauks et al. |
| 5,096,669 A | 3/1992 | Lauks et al. |
| (Continued) | | |

FOREIGN PATENT DOCUMENTS

| EP | 1481246 | 12/2004 |
| WO | 2010073182 | 7/2010 |
| WO | 2011036597 | 3/2011 |

OTHER PUBLICATIONS

Apple et al., "Determination of 19 Cardiac Troponin I and T Assay 99th Percentile Values from a Common Presumably Healthy Population", *Clinical Chemistry*, 58:11, 8 pages, 2012.
(Continued)

*Primary Examiner* — Melanie Brown
(74) *Attorney, Agent, or Firm* — Kilpatrick Townsend & Stockton LLP

(57) ABSTRACT

The present invention relates to systems and methods that utilize a combination of immunoassay and magnetic immunoassay techniques to detect an analyte within an extended range of specified concentrations. In particular, a device includes a first immunosensor including an immobilized layer of capture antibodies configured to bind to a first complex of signal antibodies and cardiac troponin such that a second complex of the first complex and the immobilized layer of capture antibodies is localized on or near the first immunosensor. The device further includes a second immunosensor having a magnetic field disposed locally around the second immunosensor. The magnetic field is configured to attract magnetic beads such that a third complex of the first
(Continued)

complex and capture antibodies immobilized on the magnetic beads is localized on or near the second immunosensor sensor.

13 Claims, 19 Drawing Sheets

(51) Int. Cl.
    *G01N 27/74*     (2006.01)
    *G01N 33/68*     (2006.01)

(52) U.S. Cl.
    CPC ... *G01N 33/5438* (2013.01); *G01N 33/54326* (2013.01); *G01N 33/54353* (2013.01); *G01N 33/6887* (2013.01); *C07K 2317/92* (2013.01); *C07K 2317/94* (2013.01); *G01N 2800/324* (2013.01); *G01N 2800/325* (2013.01)

(56) References Cited

U.S. PATENT DOCUMENTS

| | | | |
|---|---|---|---|
| 5,200,051 A | 4/1993 | Cozzette et al. | |
| 5,554,339 A | 9/1996 | Cozzette et al. | |
| 7,419,821 B2 | 9/2008 | Davis et al. | |
| 7,682,833 B2 | 3/2010 | Miller et al. | |
| 7,723,099 B2 | 5/2010 | Miller et al. | |
| 8,216,529 B2 | 7/2012 | Ade et al. | |
| 9,233,370 B2 | 1/2016 | Miller et al. | |
| 2012/0034633 A1* | 2/2012 | Miller | B01L 3/502761 435/7.94 |
| 2014/0273014 A1* | 9/2014 | Di Tullio | G01N 33/62 435/7.9 |
| 2017/0176419 A1* | 6/2017 | Li | G01N 33/54366 |

OTHER PUBLICATIONS

Sandoval and Apple, "The Global Need to Define Normality: The 99$^{th}$ Percentile Value of Cardiac Troponin", *Clinical Chemistry*, 60:3, 8 pages, 2014.

"International Search Report and Written Opinion" issued in PCT/US2017/065284, dated Mar. 5, 2018, 11 pages.

* cited by examiner

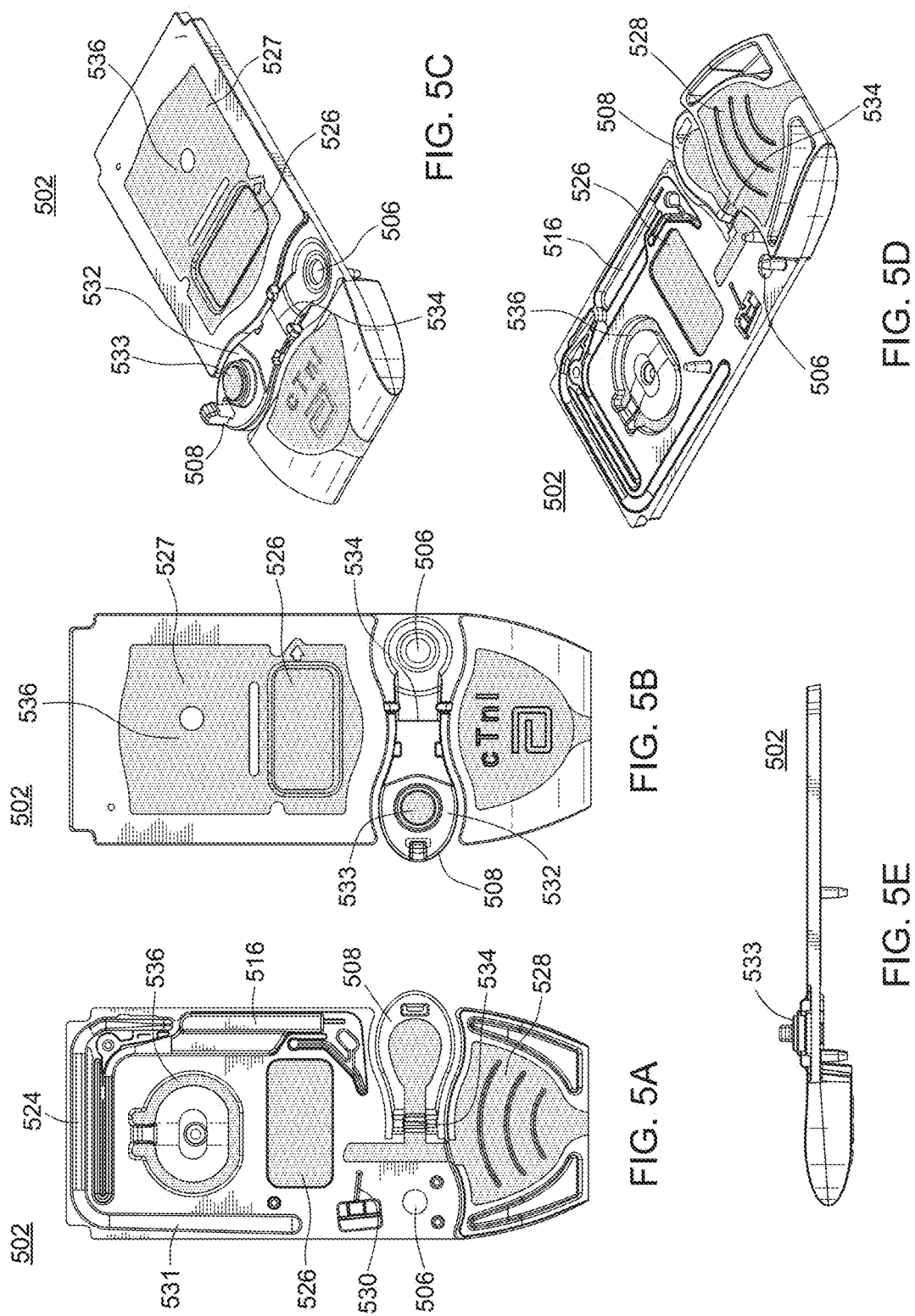

DUAL RANGE CARDIAC TROPONIN IMMUNOASSAY DEVICES AND METHODS USING IMMUNOSENSOR AND MAGNETIC IMMUNOSENSOR

CROSS-REFERENCE TO RELATED APPLICATIONS

This application claims priority to U.S. Provisional Application No. 62/432,297 filed on Dec. 9, 2016, the entirety of which is incorporated herein by reference.

FIELD OF THE INVENTION

The present invention relates to systems and methods of determining analytes in point-of-care testing. In particular, the present invention relates to systems and methods that utilize a combination of immunoassay and magnetic immunoassay techniques to detect an analyte within an extended range of specified concentrations.

BACKGROUND OF THE INVENTION

Point-of-care (POC) sample analysis systems are generally based on one or more re-usable test instruments (e.g., a reading apparatus) that perform sample tests using a single-use disposable testing device, e.g., a cartridge or strip that contains analytical elements, e.g., electrodes or optics for sensing analytes such as pH, oxygen and glucose. The disposable testing device can include fluidic elements (e.g., conduits for receiving and delivering the sample to sensing electrodes or optics), calibrant elements (e.g., aqueous fluids for standardizing the electrodes with a known concentration of analyte), and dyes with known extinction coefficients for standardizing optics. The instrument or reading apparatus contains electrical circuitry and other components for operating the electrodes or optics, making measurements, and performing computations. The instrument or reading apparatus also has the ability to display results and communicate those results to laboratory and hospital information systems (LIS and HIS, respectively), for example, via a computer workstation or other data management system. Communication between the instrument or reading apparatus and a workstation, and between the workstation and a LIS or HIS, can be via, for example, an infrared link, a wired connection, wireless communication, or any other form of data communication that is capable of transmitting and receiving electrical information, or any combination thereof. A notable point-of-care system (The i-STAT® System, Abbott Point of Care Inc., Princeton, N.J.) is disclosed in U.S. Pat. No. 5,096,669, which comprises a disposable device, operating in conjunction with a hand-held analyzer, for performing a variety of measurements on blood or other fluids.

One benefit of point-of-care sample testing systems is the elimination of the time-consuming need to send a sample to a central laboratory for testing. Point-of-care sample testing systems allow a nurse or doctor (user or operator), at the bedside of a patient, to obtain a reliable quantitative analytical result, sometimes comparable in quality to that which would be obtained in a laboratory. In operation, the nurse selects a testing device with the required panel of tests, draws a biological sample from the patient, dispenses it into the testing device, optionally seals the testing device, and inserts the testing device into the instrument or reading apparatus. While the particular order in which the steps occur may vary between different point-of-care systems and providers, the intent of providing rapid sample test results close to the location of the patient remains. The instrument or reading apparatus then performs a test cycle, i.e., all the other analytical steps required to perform the tests. Such simplicity gives the doctor quicker insight into a patient's physiological status and, by reducing the turnaround time for diagnosis or monitoring, enables a quicker decision by the doctor on the appropriate treatment, thus enhancing the likelihood of a successful patient outcome.

Cardiac marker testing such as troponin testing is one such diagnostic test that benefits from the quicker turnaround time provided via POC sample analysis systems. National and international cardiology guidelines have recommended a one-hour turnaround time for reporting results of cardiac markers such as troponin to emergency department personnel, measured from the time of blood collection to reporting. The use of POC sample analysis systems reduce the turnaround times for reporting results of cardiac markers from that of central laboratory assays, but current POC sample analysis systems are not as precise or sensitive as central laboratory assays. In fact, the gap in precision and sensitivity between central laboratory assays and POC sample analysis systems is growing as manufacturers of central laboratory assays have or will release troponin assays that have a $99^{th}$ percentile cutoff of about 10 ng/L and a limit of detection of <1 ng/L, which is presently not possible for current POC testing assays. These high-sensitivity assays are able to detect troponin in the majority of healthy subjects, and clinically, this allows for the detection of more cases of myocardial injury.

In order to compete analytically with these central laboratory assays, next generation POC testing assays will need to make technologic advancements. Thus there remains a need for systems and methods to extend the range of sensitivity for sample testing devices, e.g., single-use blood testing cartridges, used with one or more test instruments at the POC in a hospital or other location for delivering medical care.

SUMMARY OF THE INVENTION

In one embodiment, a device is provided for detecting cardiac troponin in a biological sample. The device includes a first immunosensor including an immobilized layer of capture antibodies configured to bind to a first complex of signal antibodies and the cardiac troponin such that a second complex of the first complex and the immobilized layer of capture antibodies is localized on or near the first immunosensor, and second immunosensor having a magnetic field disposed locally around the second immunosensor, wherein the magnetic field is configured to attract magnetic beads such that a third complex of the first complex and capture antibodies immobilized on the magnetic beads is localized on or near the second immunosensor sensor. The first immunosensor is configured to generate a first signal indicative of a concentration of the cardiac troponin from a reaction of a signal agent with the second complex. The second immunosensor is configured to generate a second signal indicative of a concentration of the cardiac troponin from a reaction of the signal agent with the third complex. The first immunosensor determines the concentration of the cardiac troponin in a first range above about 2000 pg/mL based on the first signal. The second immunosensor determines the concentration of the cardiac troponin in a second range from about 0 to about 250 pg/mL based on the second signal. A combination of the first immunosensor and the second immunosensor determines the concentration of the cardiac troponin in a third range from about 250 to about 2000 pg/mL based on the first signal and the second signal.

Optionally, the cardiac troponin is cardiac troponin I (cTnI), and the device further includes a first reagent region coated with the signal antibodies for the cardiac troponin and a second reagent region coated with the magnetic beads. The first reagent region, the second reagent region, the first immunosensor, and the second immunosensor are located on a substrate.

In another embodiment, a method is provided that includes measuring a first signal at a first immunosensor from a reaction of a signal agent with a first complex of signal antibodies, cardiac troponin, and capture antibodies immobilized on a surface of the first immunosensor, measuring a second signal at a second immunosensor from a reaction of the signal agent with a second complex of the signal antibodies, the cardiac troponin, and capture antibodies immobilized on magnetic beads that are localized on or near a surface of the second immunosensor via a magnetic field, determining a first concentration of the cardiac troponin in a sample from the first signal, determining a second concentration of the cardiac troponin in the sample from the second signal, and comparing the first concentration and the second concentration to a predetermined crossover concentration point. When the first concentration is greater than the crossover concentration point, the first concentration is reported as a final concentration of the cardiac troponin in a first range above about 1000 pg/mL. When the second concentration is less than the crossover concentration point, the second concentration is reported as the final concentration of the cardiac troponin in a second range from about 0 to about 1000 pg/mL.

Optionally, the first immunosensor and the second immunosensor are electrochemical immunosensors and the first signal and the second signal are electrochemical signals.

In some embodiments, the signal antibodies are conjugated with an enzyme such as alkaline phosphatase, and the substrate is a phosphorylated molecule configured such that when a phosphate moiety is removed the molecule becomes electroactive.

In another embodiment, a method is provided that includes measuring a first signal at a first immunosensor from a reaction of a signal agent with a first complex of signal antibodies, cardiac troponin, and capture antibodies immobilized on a surface of the first immunosensor, measuring a second signal at a second immunosensor from a reaction of the signal agent with a second complex of the signal antibodies, the cardiac troponin, and capture antibodies immobilized on magnetic beads that are localized on or near a surface of the second immunosensor via a magnetic field, determining a first concentration of the cardiac troponin in a sample from the first signal, determining a second concentration of the analyte in the sample from the second signal, determining a weighted average of the first concentration and the second concentration, and comparing the weighted average of the first concentration and the second concentration to a predetermined crossover concentration zone from about 250 to about 2000 pg/ml. When the weighted average is above the crossover concentration zone, a first concentration is reported in a first range above about 2000 pg/mL as a final concentration of the cardiac troponin. When the weighted average is below the crossover concentration zone, a second concentration is reported in a second range from about 0 to about 250 pg/mL as the final concentration of the cardiac troponin. When the weighted average is within the crossover concentration zone, the weighted average is reported as the final concentration of the cardiac troponin.

Optionally, the first immunosensor and the second immunosensor are electrochemical immunosensors and the first signal and the second signal are electrochemical signals.

In some embodiments, the signal antibodies are conjugated with an enzyme such as alkaline phosphatase, and the substrate is a phosphorylated molecule configured such that when a phosphate moiety is removed the molecule becomes electroactive.

BRIEF DESCRIPTION OF THE DRAWINGS

The present invention will be better understood in view of the following non-limiting figures, in which:

FIGS. 4 and 5A-5J show sensing devices or cartridges in accordance with some aspects of the invention;

DETAILED DESCRIPTION OF THE INVENTION

Introduction

Cardiac troponin (cTn) is the primary biomarker used in the diagnosis of acute myocardial infarction (AMI) and risk stratification for future adverse cardiac events. However, the analytical sensitivity gap between central laboratory assays and POC sample analysis systems for cardiac troponin testing has grown and can hinder the adoption of POC testing for some hospitals. There may also be a need for POC sample analysis systems that can detect other biomarkers or multiple biomarkers. For example, while cardiac troponin is the primary analyte for AMI diagnosis, B-type natriuretic peptide (BNP) and NT-proBNP have shown to be useful for short-term risk stratification. The detection of high sensitivity cardiac troponin (hs-cTn) might also be useful as a risk stratification marker in primary care, i.e., for patients who are asymptomatic. This is based on observations that increased cardiac troponin is associated with a high risk for adverse cardiac outcomes in the absence of acute coronary syndromes. If detection of these biomarkers becomes adopted as part of routine medical care for high risk patients, then POC testing for hs-cTn may be useful and convenient when tested in physician offices and clinics.

Troponins are generally undetectable in healthy patients. The absolute abnormal value for troponins varies depending on the clinical setting in which the patient is evaluated and the assay used. In a patient who presents with chest pain and possible myocardial infarction (MI), an abnormal value is typically above the $99^{th}$ percentile of the healthy population as a cutoff using an assay with acceptable precision. The $99^{th}$ percentiles for cTnT and cTnI detection are well known as 0.012 to 0.016 ng/mL and 0.008 to 0.058 ng/mL, respectively. The wider range of the $99^{th}$ percentile concentrations for the cTnI assay stems from the many different detection assays using different antibodies and assay approaches. POC cTn assays often have higher $99^{th}$ percentile values due in part to increased analytical noise and lower sensitivity as compared to the current laboratory cTn assays. For example, the $99^{th}$ percentile cutoff point for cTnT detection in central laboratory assays is well-known at 0.01 ng/mL. In contrast, the $99^{th}$ percentile cutoff point for cTnT detection in troponin POC sample analysis systems is typically around 0.05 to 0.08 ng/mL.

Figure 1:
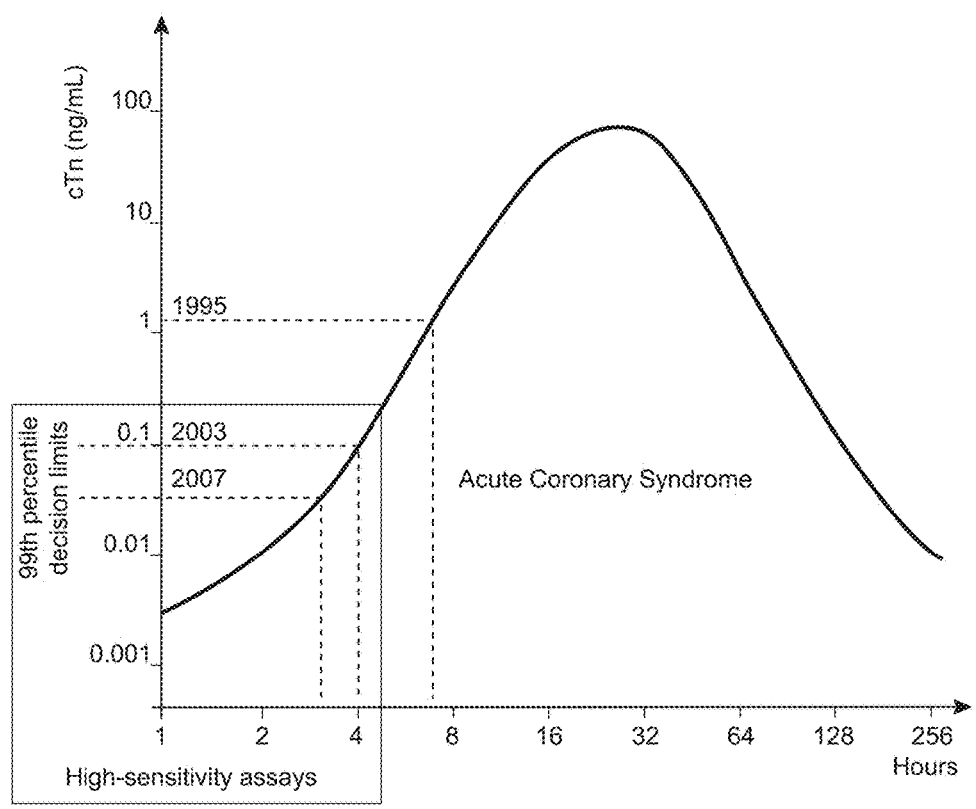
FIG. 1 illustrates the evolution of Troponin immunoassays in accordance with some aspects of the invention.

Troponin POC sample analysis systems are typically based on the reaction of the analyte with antibodies. Within the finite limits of the detection zone, the analytical sensitivity is a direct function of the ability of the assay to capture as much of the analyte as possible with optimal precision. Optimal precision, as described by the coefficient of variation (CV) at the $99^{th}$ percentile of the upper reference limit for each assay (as shown in FIG. 1), is generally defined as less than or equal to ten percent. Better precision (CV of less than or equal to ten percent) allows for more sensitive assays and facilitates the detection of changing values and lowers the $99^{th}$ percentile decision limits of the assay. Nonetheless, developing POC sample analysis systems that meet these needs and lowers the $99^{th}$ percentile decision limits of the assay has been challenging.

Enhancement of assay performance requires increasing the resolution between (i) the limit of blank (LoB) and the limit of detection (LoD) and (ii) the LoD and the $99^{th}$ percentile. LoB is the highest apparent analyte concentration expected to be found when replicates of a blank sample containing no analyte are tested. LoD is the lowest analyte concentration likely to be reliably distinguished from the LoB and at which detection is feasible. LoD is determined by utilizing both the measured LoB and test replicates of a sample known to contain a low concentration of analyte. Limit of Quantitation (LoQ) is the lowest concentration at which the analyte can not only be reliably detected but at which some predefined goals for bias and imprecision are met. The LoQ may be equivalent to the LoD or it could be at a much higher concentration. Sensitivity, analytical sensitivity, lower limit of detection, LoB, LoD, and LoQ are all terms used to describe the smallest concentration of an analyte that can be reliably measured by the assay.

One of the ways to improve the sensitivity or increase the resolution between (i) the LoB and the LoD and (ii) the LoD and the $99^{th}$ percentile in an immunoassay is to improve the signal to noise ratio. For example, improvement to sensitivity in an immunoassay may be achieved by increasing the signal generating ability of the system or decreasing the background signal generated by the system. The signal generating ability may be considered in terms of the "sensitivity slope" or the amount of signal generated per unit of analyte: slope=(Current (nA))/(Concentration (ng/ml)), and thus the Concentration (ng/ml)=(Current (nA))/(slope (nA/ng/ml). In conventional POC sample analysis systems such as those described in U.S. Pat. No. 7,419,821, which is incorporate herein by reference in its entirety, a sensor is coated with a biolayer comprising a covalently attached anti-troponin antibody, to which a complex of troponin and enzyme-antibody conjugate binds. The enzyme-antibody conjugate is thereby immobilized close to the electrode in proportion to the amount of troponin initially present in the sample. In addition to specific binding, the enzyme-antibody conjugate may bind non-specifically to the sensor. Non-specific binding provides a background signal from the sensor that is undesirable and should be minimized. To solve this problem, U.S. Pat. No. 7,419,821 discloses the use of rinsing protocols, and in particular the use of segmented fluid to rinse the sensor, as a means to decrease the background signal. POC sample analysis systems such as those described in U.S. Pat. No. 7,419,821 have a signal generating ability or "sensitivity slope" of about 4 nA/ng/ml and are particularly effective for the detection of high levels of a biomarker such as troponin (i.e., high-end sensitivity).

However, based on a sample size of 10 μL, which is typically of POC sample analysis systems, and a number of analyte molecules that may be present in such a sample size, the theoretical maximum slope is about 1200 nA/ng/mL. It is believed that the conventional POC sample analysis systems merely have a signal generating ability of about 4 nA/ng/ml because the biolayer comprising the covalently attached anti-troponin antibody is immobilized on, or close to, the sensor surface, and thus only analyte brought into contact with the sensor surface is subject to capture and analysis (e.g., an estimated 0.3% of all analyte in the sample is subject to capture and analysis).

In order to increase the signal generating ability or "sensitivity slope" beyond 4 nA/ng/ml and increase the effectiveness of an immunoassay for the detection of low levels of a biomarker such as troponin (i.e., low-end sensitivity), conventional POC sample analysis systems such as those described in U.S. Pat. No. 9,233,370, which is incorporate herein in its entirety, were developed with magnetically susceptible bead capture techniques. The magnetically susceptible bead capture techniques allow for the enzyme-antibody conjugate to be localized on, or close to, the sensor surface and function to substantially retain the enzyme-antibody conjugate at or near the sensor during removal of the unbound sample and washing of the sensor to remove the non-specific binding. POC sample analysis systems such as those described in U.S. Pat. No. 9,233,370 have a signal generating ability or "sensitivity slope" of about 40 nA/ng/ml (i.e., 10× the signal generating ability of non-magnetic immunoassays) and are particularly effective for the detection of low levels of a biomarker such as troponin (i.e., low-end sensitivity). Nonetheless, conventional POC sample analysis systems are far from achieving the theoretical maximum slope of about 1200 nA/ng/mL.

In order to improve upon the signal generating ability of conventional POC sample analysis systems and increase the effectiveness of an immunoassay for the detection of low levels of a biomarker such as troponin (i.e., low-end sensitivity), one embodiment of the present invention is directed to an extended range magnetic sensor device having a fixed antibody capture site situated over a first sensor (e.g., an amperometric sensor) and another antibody capture site situated over a second sensor (e.g., an amperometric sensor) with a high field magnet positioned underneath. The two sensors each have sensitivity to an analyte (e.g., cTn) but with different sensitivities due to the difference in the capture reagents being used for each respective sensor. The first sensor is typically the lower sensitivity sensor (a slope of less than 5 nA/ng/ml) and is particularly effective for the detection of high levels of an analyte such as troponin (i.e., high-end sensitivity). The second sensor is typically the higher sensitivity sensor (a slope of greater than 7 nA/ng/ml) and is particularly effective for the detection of low levels of an analyte such as troponin (i.e., low-end sensitivity). Consequently, the implementation of both the lower sensitivity sensor and the high sensitivity sensor on a single device extends the range of concentrations of an analyte that may be detected using the device.

The difference in the location of the analyte and label reagent binding between the two sensors accounts largely for their difference in sensitivities to the analyte. The sensitivity differences between the two sensors may be further controlled by variation of the time between the dissolution of the paramagnetic reagent into the sample and the sample's positioning over the first sensor. Further control of the sensitivities between the two sensors may be achieved by altering the concentration of the paramagnetic antibody coated particles used in the assay. Another technique of controlling the sensor sensitivities may be through control of antibody concentration, affinities or avidities on the first sensor and the paramagnetic reagents.

The advantage of the aforementioned technical solution for improving upon the signal generating ability of POC sample analysis systems and increasing the effectiveness of an immunoassay for the detection of low levels of a biomarker such as troponin (i.e., low-end sensitivity) is that it will eliminate the technical problems with increasing the resolution between (i) the limit of blank (LoB) and the limit of detection (LoD) and (ii) the LoD and the $99^{th}$ percentile. For example, implementations of the present invention provide a technical contribution over conventional POC sample analysis systems and methods because the technical features of the present invention interoperate to provide both the lower sensitivity sensor and the high sensitivity sensor on a single device, which extends the range of concentrations of an analyte that may be detected using the device.

Immunoassays

Figure 2:
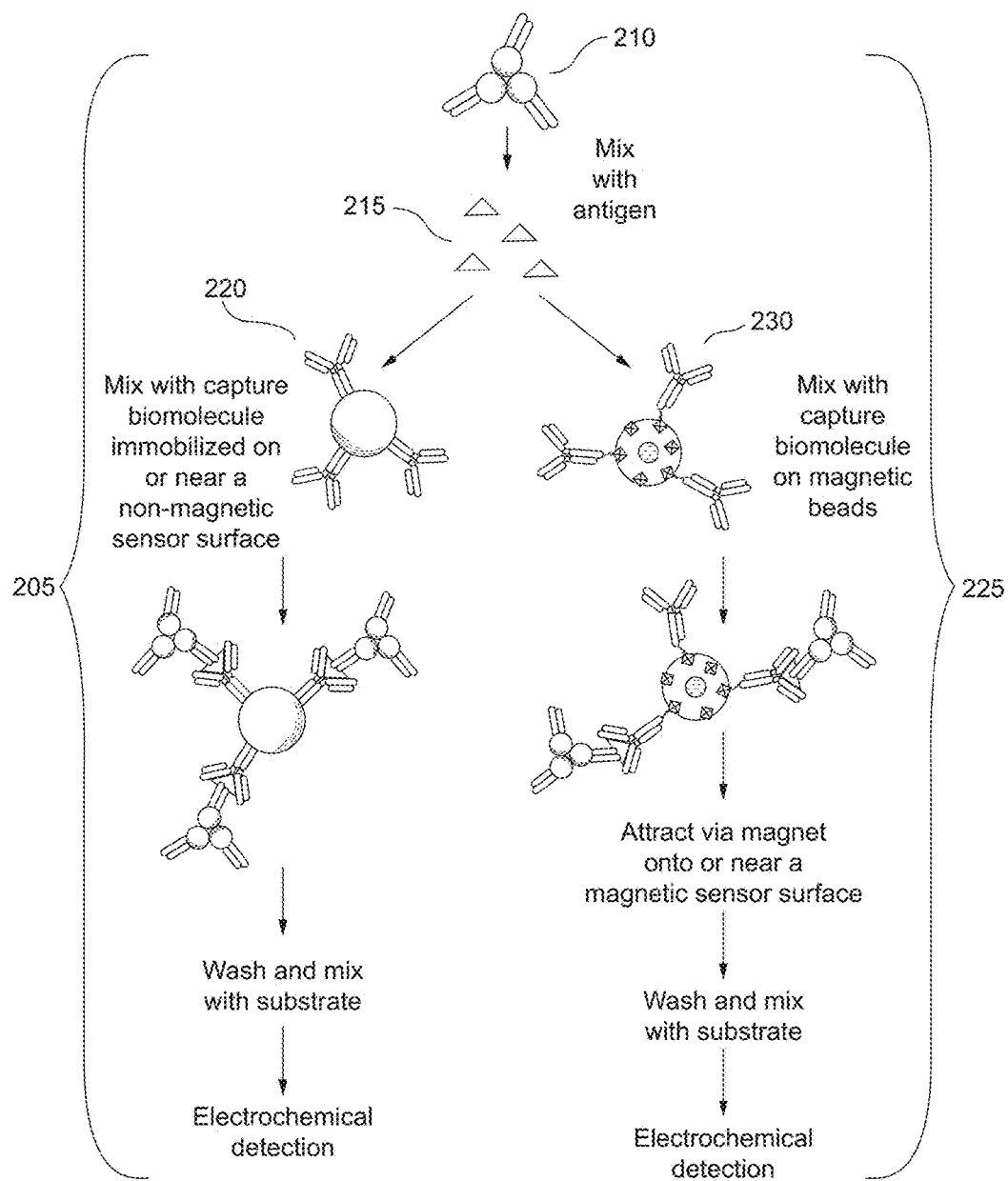
FIG. 2 illustrates the principle of a combined immunoassay accordance with some aspects of the invention.

FIG. 2 illustrates the principle of a combined immunoassay (e.g., a one-step combined immunoassay) 200 according to specific embodiments of the present invention that extends the range of concentrations of a target analyte such as troponin I (TnI) or cardiac troponin I (cTnI), which may be detected using an analyzer. In various embodiments, the combined immunoassay 200 includes a non-magnetic immunoassay technique 205 that utilizes an enzyme-biomolecule conjugate 210 configured to bind to the target analyte 215 and a capture biomolecule 220 (e.g., latex beads or microspheres coated with capture biomolecule) immobilized on or near a surface of a non-magnetic sensor (i.e., a heterogeneous surface capture immunosensor). The capture biomolecule 220 is configured to bind to the target analyte 215 that is bound to the enzyme-biomolecule conjugate 210 such that the enzyme-biomolecule conjugate 210 is captured and immobilized on or near a surface of the non-magnetic sensor. The non-magnetic sensor may be either clamped at a fixed electrochemical potential sufficient to oxidize or reduce a product of a hydrolyzed substrate but not the substrate directly, or the potential may be swept one or more times through an appropriate range. The combined immunoassay 200 further includes a magnetic immunoassay technique 225 that utilizes the enzyme-biomolecule conjugate 210 configured to bind to the target analyte 215 and a capture biomolecule 230 (e.g., magnetic beads or microspheres coated with capture biomolecule). The capture biomolecule 230 is configured to bind to the target analyte 215 that is bound to the enzyme-biomolecule conjugate 210. The capture biomolecule 230 bound to the target analyte 215 that is bound to the enzyme-biomolecule conjugate 210 may be attracted via a magnet onto or near a surface of a magnetic sensor (i.e., a homogeneous magnetic bead capture immunosensor) such that the enzyme-biomolecule conjugate 210 is captured and immobilized on or near a surface of the magnetic sensor. The magnetic sensor may be either clamped at a fixed electrochemical potential sufficient to oxidize or reduce a product of a hydrolyzed substrate but not the substrate directly, or the potential may be swept one or more times through an appropriate range.

The enzyme-biomolecule conjugate 210 includes an enzyme conjugated to biomolecules selected to bind to an analyte of interest. In some embodiments, the enzyme is alkaline phosphatase (ALP), horseradish peroxidase, or glucose oxidase and the biomolecules are chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. In some embodiments, the biomolecules may be selected to bind to one or more of human chorionic gonadotrophin, troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. For example, the biomolecules may be selected as a monoclonal or polyclonal anti-troponin I antibody (e.g., BiosPacific—Peptide 4 (G-130-C), HyTest —560 (19C7, Cat#4T21—monoclonal Troponin I Ab) and International Point of Care—817 (Cat# MA-1040). In certain embodiments, the biomolecule binds to the analyte specifically and has an affinity constant for binding analyte ligand of about $10^7$ to $10^{15}$ $M^{-1}$.

The capture biomolecule 220 may be provided as a biolayer deposited onto or near at least a portion of the non-magnetic sensor. A biolayer is a porous layer comprising on its surface a sufficient amount of biomolecules that can either bind to an analyte of interest, or respond to the presence of such analyte by producing a change that is capable of measurement. Optionally, a permselective screening layer may be interposed between the non-magnetic sensor and the biolayer to screen electrochemical interferents as described in U.S. Pat. No. 5,200,051, which is incorporated herein in its entirety.

In some embodiments, the biolayer is constructed from latex beads of specific diameter in the range of about 0.001 to 50 microns (e.g., ThermoFisher OptiLink Carboxylate-Modifies Microparticles (Catalog#83000591100351), 0.2 um diameter). The beads may be modified by covalent attachment of any suitable biomolecules that can either bind to an analyte of interest, or respond to the presence of such analyte by producing a change that is capable of measurement. Many methods of attachment exist in the art, including providing amine reactive N-hydroxysuccinimide ester groups for the facile coupling of lysine or N-terminal amine groups of proteins. In certain embodiments, the biomolecules are chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. In some embodiments, the biomolecules may be selected to bind one or more of human chorionic gonadotrophin, troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. For example, the biomolecules may be selected as a monoclonal or polyclonal anti-troponin I antibody (e.g., SDIX—M06 (# D2440MA06-MA) and HyTest—Cap1 (19C7, Cat#4T21—monoclonal Troponin I Ab). In certain embodiments, the biomolecule binds to the analyte specifically and has an affinity constant for binding analyte ligand of about $10^7$ to $10^{15}$ $M^{-11}$.

The capture biomolecule 230 may be provided as biomolecules attached to magnetically susceptible beads. The magnetically susceptible beads may be comprised of any material known in the art that is susceptive to movement by a magnet (e.g., permanent magnet or electromagnet) utilized in or in concert with the device of the present invention. As such, the terms "magnetic" and "magnetically susceptible" with regard to beads can be used interchangeably.

In some embodiments, the beads include a magnetic core, which preferably is completely or partially coated with a coating material. The magnetic core may comprise a ferromagnetic, paramagnetic or a superparamagnetic material. In preferred embodiments, the magnetically susceptible beads comprise a core and an outer polymer coating. In other embodiments, the magnetic beads comprise non-magnetic substrate beads formed, for example, of a material selected from the group consisting of polystyrene, polyacrylic acid and dextran, upon which a magnetic coating is placed. In certain embodiments where the magnetically susceptible beads comprise a core, the magnetic core may comprise one or more of ferrite, Fe, Co, Mn, Ni, metals comprising one or more of these elements, ordered alloys of these elements, crystals comprised of these elements, magnetic oxide structures, such as ferrites, and combinations thereof. In other embodiments where the magnetically susceptible beads comprise a core, the magnetic core may be comprised of magnetite ($Fe_3O_4$), maghemite ($\gamma$-$Fe_2O_3$), or divalent metal-ferrites provided by the formula $Me_{1-x}OFe_3+xO_3$ where Me is, for example, Cu, Fe, Ni, Co, Mn, Mg, or Zn or combinations of these materials, and where x ranges from 0.01 to 99. Suitable materials for the outer polymer coating over the core include synthetic and biological polymers, copolymers and polymer blends, and inorganic materials. Polymer materials may include various combinations of polymers of acrylates, siloxanes, styrenes, acetates, akylene glycols, alkylenes, alkylene oxides, parylenes, lactic acid, and glycolic acid. Biopolymer materials include starch or similar carbohydrate. Inorganic coating materials may include any combination of a metal, a metal alloy, and a ceramic. Examples of ceramic materials may include hydroxyapatite, silicon carbide, carboxylate, sulfonate, phosphate, ferrite, phosphonate, and oxides of Group IV elements of the Periodic Table of Elements.

In principle, any correctly-sized magnetically susceptible bead capable of being positioned with the magnet of the present invention may be utilized, taking into account the dispersability requirements for the magnetically susceptible beads. In preferred embodiments, at least 50 wt. %, e.g., at least 75 wt. %, of the magnetically susceptible beads are retained at or near the sensor surface. In some exemplary embodiments, the average particle size of the magnetically susceptible beads may range from 0.01 μm to 20 μm, e.g., from 0.1 μm to 10 μm, from 0.1 μm to 5 μm or from 0.2 μm to 1.5 μm. As used herein, the term "average particle size" refers to the average longest dimension of the particles, e.g., beads, for example the diameter for spherical particles, as determined by methods well-known in the art. The particle size distribution of the magnetically susceptible beads preferably is unimodal, although polymodal distributions may also be used in accordance with the present invention. While use of a spherical magnetically susceptible bead is preferred, in other embodiments, other bead shapes and structures, e.g., ovals, sub-spherical, cylindrical and other irregular shaped particles, are within the meaning of the term "beads" and "microparticles" as used herein.

Commercial sources for magnetically susceptible bead preparations include Invitrogen™ (Carlsbad, Calif., U.S.A.) by Life Technologies™, Ademtech (Pessac, France), Chemicell GmbH (Berlin, Germany), Bangs Laboratories, Inc.™ (Fishers, Ind.) and Seradyn, Inc. (Indianapolis, Ind.) (e.g., Invitrogen™ by Life™ Technologies—Dynabeads® MyOne™ Streptavidin T1 (Catalog#65601/65602), 1 um diameter). Many of the commercially available products incorporate surface functionalization that can be employed to immobilize biomolecules such as antibodies (e.g., IgG) on the bead surfaces. Exemplary functionalizations include carboxyl, amino or streptavidin-modified magnetically susceptible beads.

In some embodiments, the magnetically susceptible beads are coated with any suitable biomolecules that can either bind to an analyte of interest, or respond to the presence of such analyte by producing a change that is capable of measurement. Many methods of attachment exist in the art, including providing amine reactive N-hydroxysuccinimide ester groups for the facile coupling of lysine or N-terminal amine groups of proteins. In the instance of streptavidin-modified magnetically susceptible beads, the biomolecules may be modified to include a binder such as biotin to attach the biomolecules on the bead surfaces. For example, the biomolecules may be attached to biotin (e.g., Thermo Scientific—EZ-link Sulfo-NHS-LC-LC-biotin (Product#21338) or EZ-link Sulfo-NHS-LC-biotin (Product#21335)). In certain embodiments, the biomolecules are chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. The biomolecules may be selected to bind one or more of human chorionic gonadotrophin, troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. For example, the biomolecules may be selected as a monoclonal or polyclonal anti-troponin I antibody (e.g., BiosPacific—Peptide 3 (G-129-C) and HyTest—Cap1 (19C7, Cat#4T21—monoclonal Troponin I Ab). In certain embodiments, the biomolecule binds to the analyte specifically and has an affinity constant for binding analyte ligand of about $10^7$ to $10^{15}$ $M^{-11}$.

As should be understood, embodiments of the present invention may be implemented in a variety of different systems and contexts. Certain embodiments are particularly applicable to immunoassays that detect an enzymatically produced electroactive species (e.g., 4-aminophenol) from the reaction of a substrate (e.g., 4-aminophenylphosphate) with the antibody-enzyme conjugate (e.g., one or more antibodies bound to alkaline phosphatase (ALP). However, the systems and techniques described herein may be used to detect an analyte using biomolecules other than antibodies labeled with various labels beyond enzymes. For example, the biomolecules described herein may be attached to labels including a radiolabel, chromophore, flurophore, chemiluminescent species, ionophore, electroactive species and others known in the art without departing from the spirit and scope of the present invention.

As should be further understood, embodiments of the present invention may be implemented in a variety of different systems and configurations, and the term on or near a surface of the sensor is used herein to describe the relationship between a biomolecule complex and the surface of a particular sensor. On or near a surface of a sensor defines a working distance between the biomolecule complex and the surface of the particular sensor that needs to be maintained such that a signal generated by a reaction of the biomolecule complex with a substrate can be measured at the surface of the particular sensor. In some embodiments, the working distance is less than 800 µm, for example less than 600 µm or less than 500 µm.

Biological Sample Test System for Performing Immunoassays

The present invention relates to a handheld POC instrument system including a self-contained disposable sensing device or cartridge (device(s)) and a reader or analyzer (instrument(s)) configured for use at a patient bedside. A fluid sample to be measured is drawn into a sample entry orifice or port in the cartridge and the cartridge is inserted into the analyzer through a slotted opening or port. Measurements performed by the analyzer are output to a display or other output device, such as a printer or data management system via a port on the analyzer to a computer port. Transmission can be via Wi-Fi, Bluetooth link, infrared and the like. For example, the handheld IVD instrument system may be of similar design to the systems disclosed in U.S. Pat. Nos. 5,096,669 and 7,419,821, both of which are incorporated herein by reference in their entireties.

Figure 3:
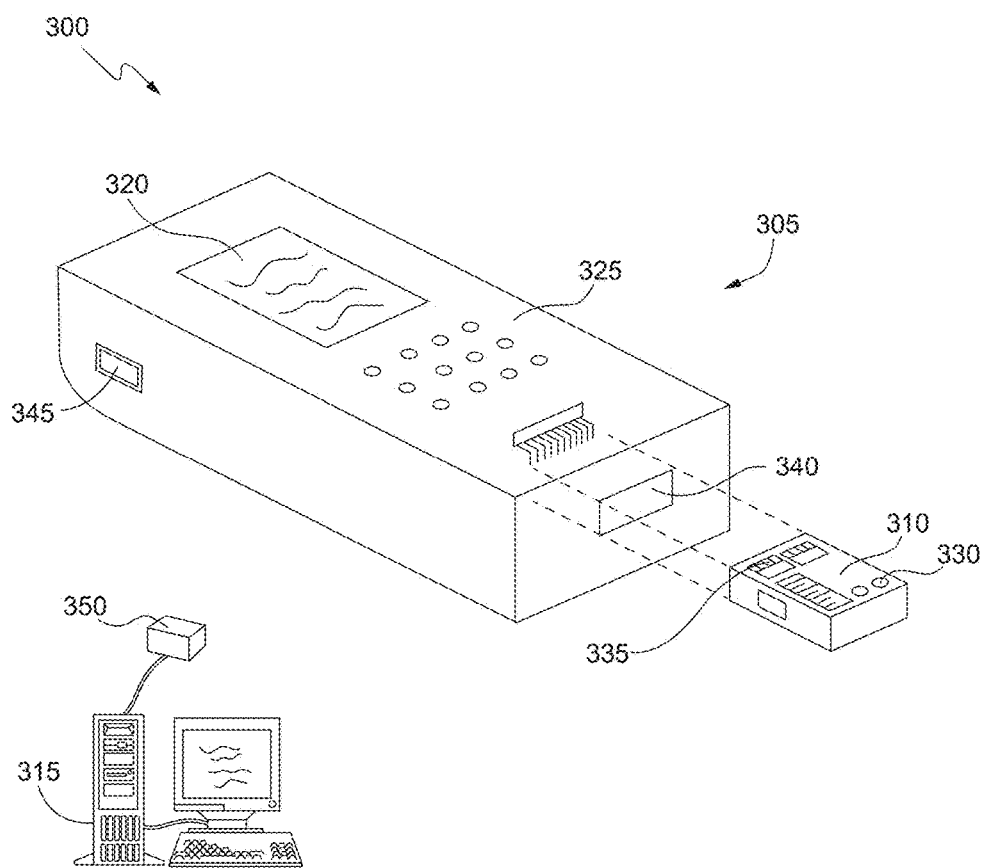
FIG. 3 shows a point-of-care instrument system in accordance with some aspects of the invention.

FIG. 3 shows the component parts and interactions of a typical handheld POC instrument system. The system 300 may include an analyzer 305, a disposable sensing device 310, and a central data station or data manager 315. The analyzer 305 may include, for example, a display 320 for visual reference and one or more input devices 325 for data entry. The one or more input devices 325 may include one or more mechanisms that permit an operator to input information to analyzer 305, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The sensing device 310 may include, for example, a port 330 for receiving a patient sample and a sensor array 335 for detecting an analyte in a biological sample. For example, the sensing device 310 may be configured to perform analyses on a range of biological sample types. These sample types may include, for example, blood, plasma, serum, sputum, cerebrospinal fluid, tears, urine, body tissue, fecal matter, and the like. The sensing device 310 may be inserted into the analyzer 305 through an opening 340 such that the analyzer 305 is in electrical contact with the sensing device 310 for implementing the functionality, steps, and/or performance of the present invention.

The analyzer 305 may communicate with the data manager 315 using, for example, a wireless connection, an infrared link, an optical link, a network connection 345, 350, or any other form of communication link that uses any form of communication protocol to transfer information. The data manager 315 can be resident on a network infrastructure such as within a cloud environment, or may be a separate independent computing device (e.g., a computing device of a service provider). The data manager 315 may include a bus, processor, a storage device, a system memory (hardware device), one or more input devices, one or more output devices, and a communication interface. The data manager 315 may be configured to provide connectivity between the analyzer 305 and central locations, such as, for example, a LIS or HIS (laboratory or hospital information system), and sensing device 305. The data manager 315 may be connected with the various system constituents using any type of communications connection that is capable of transmitting and receiving electronic information, such as, for example, an Ethernet connection or other computer network connection. The data manager 315 can also optionally provide a direct link back to a vendor's (product manufacturer) information system, for example via the Internet, a dial-up connection or other direct or indirect communication link, or through the LIS or HIS. Such an exemplary embodiment can provide for automated re-ordering of sensing devices 305 to maintain predetermined levels of inventory at a hospital and allow the vendor to forecast demand and adequately plan the manufacture of the devices 305. It can also provide a means for updating device information, e.g. cartridge attributes and profiles, and control fluid information, e.g. expected analyte test ranges.

The analyzer 305 may further include a processor, a storage device, and system memory. The processor may be one or more conventional processors, microprocessors, or specialized dedicated processors that include processing circuitry operative to interpret and execute computer readable program instructions, such as program instructions for controlling the operation and performance of one or more of the various other components of the analyzer 305 and/or sensing device 310 for implementing the functionality, steps, and/or performance of the present invention. In certain embodiments, the processor interprets and executes the processes, steps, functions, and/or operations of the present invention, which may be operatively implemented by the computer readable program instructions. For example, the processor can measure a signal generated at a sensor of the sensing device 310 (e.g., a signal indicative of the presence and/or concentration of an analyte in a biological sample), determine a concentration of the analyte in the biological sample based on the measured signal, and report the determined concentration (e.g., display the determined concentration on display 320). In some embodiments, the information obtained or generated by the processor, e.g., the identity of the sensing device 310, the shelf-life of the sensing device 310, the determined concentration, etc., can be stored in the storage device.

The storage device may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of analyzer 305 in accordance with the different aspects of the present invention. In embodiments, storage device may store an operating system, application programs, and program data in accordance with aspects of the present invention.

The system memory may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system (BIOS) including the basic routines that help to transfer information between the various other components of the analyzer 305 and system 300, such as during start-up, may be stored in the ROM. Additionally, data and/or program modules, such as at least a portion of operating system, program modules, application programs, and/or program data, that are accessible to and/or presently being operated on by the processor, may be contained in the RAM. In embodiments, the program modules and/or application programs can comprise a lookup table, an algorithm such as an algorithm to identify for determining a concentration of an analyte over an extended concentration range, and a comparison tool, which provides the instructions for execution of processor.

The analyzer 305 may further include a barcode reader for reading information from a patient's bar-coded wristband, from a barcode on a sensing device 310 or from any other item (e.g., a box of sensing devices, box of control fluids, etc.) used in conjunction with the analyzer 305. Other such encoding arrangements can be used. For example, the analyzer 305 may also include (either alternatively or in addition to the barcode reader) a radio-frequency (RF) identification device that is capable of identifying an RF tag that is contained on or in each individual sensing device or each box of devices. According to another exemplary embodiment of the present invention, one or more of the encoding arrangements may be based upon a binary coding pin array of the type disclosed in, for example, U.S. Pat. No. 4,954,087, which is incorporated herein by reference in its entirety. The various encoding arrangements may convey relevant information such as, for example, the identity of a specific device type, date and location of manufacture, manufacturing lot number, expiration date, a unique number associated with a device, coefficients for use by the analyzer 305 associated with the calculation of blood or other sample parameters, and the like.

Sensing Device or Cartridge

Figure 4:
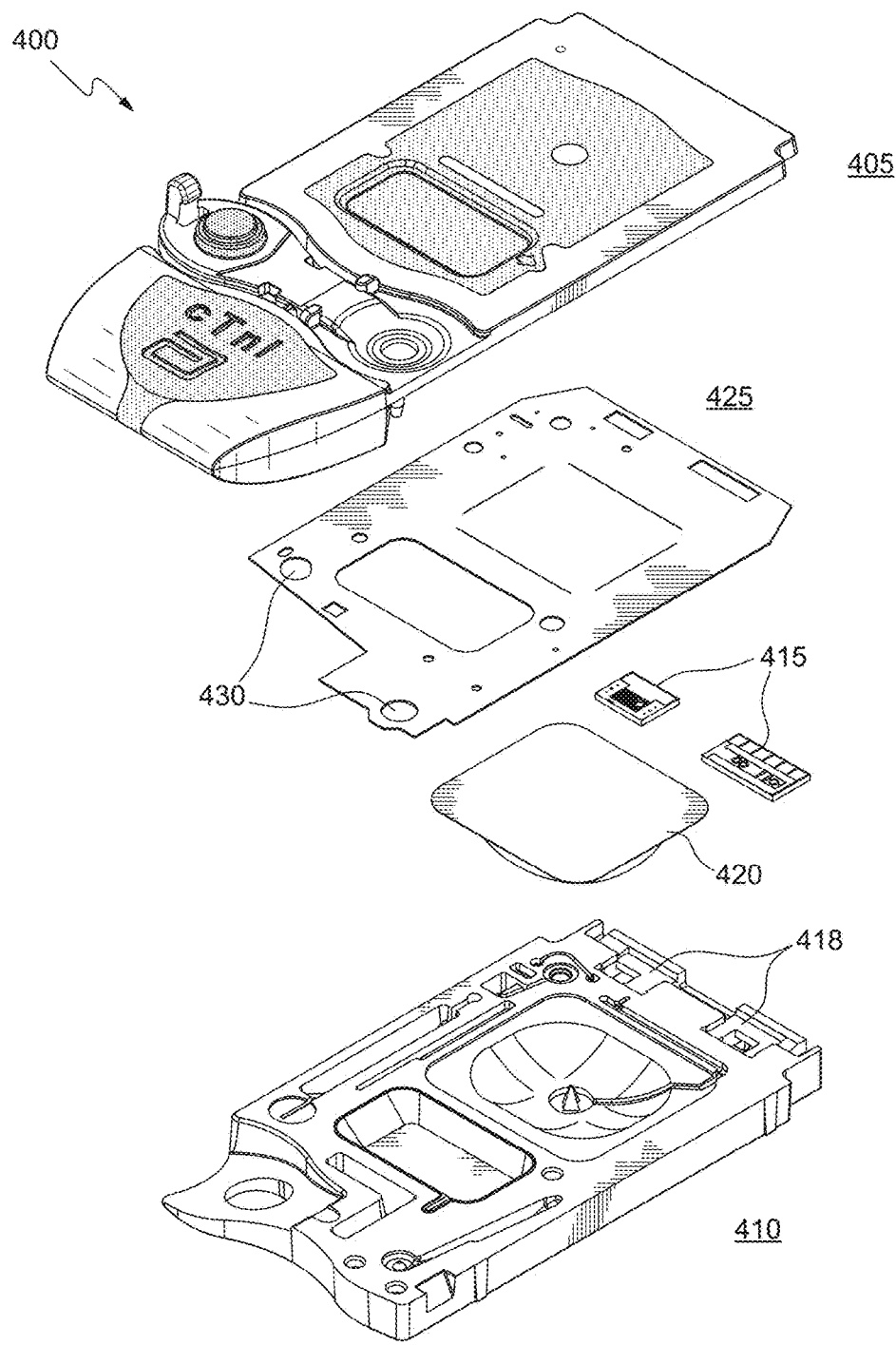
Figure 5H:
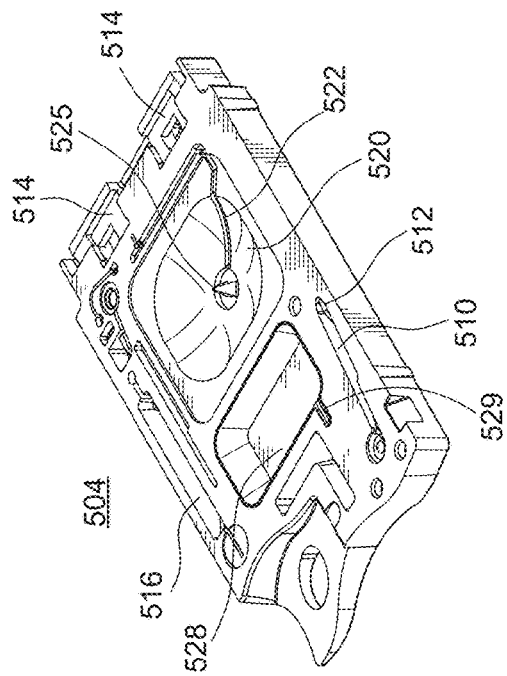
Figure 5I:
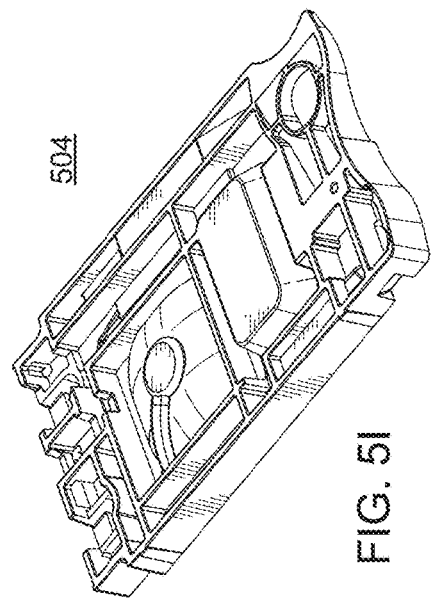
Figure 5G:
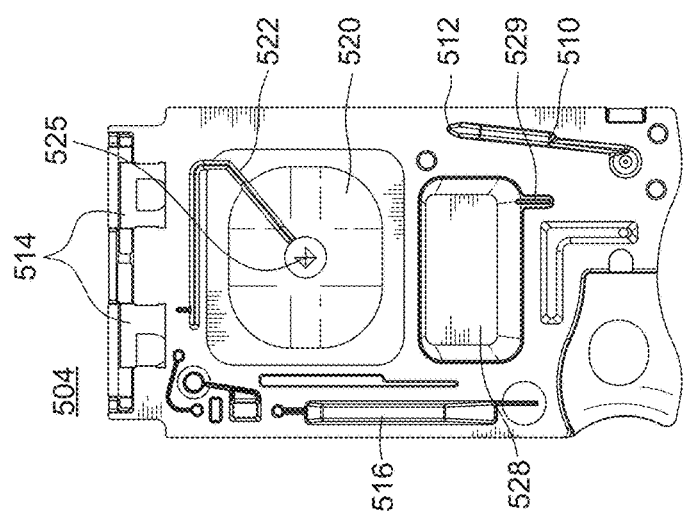
Figure 5F:
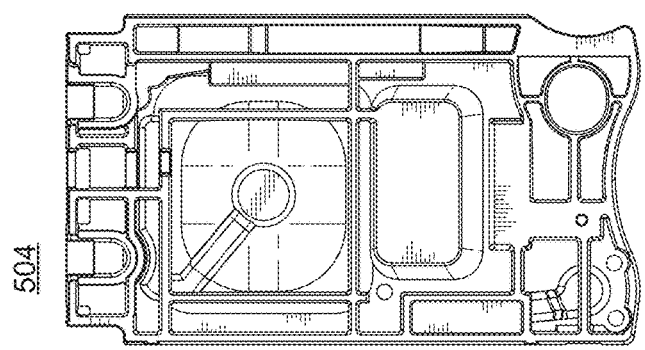
Figure 5J:

In one embodiment, as shown in FIG. 4, a sensing device or cartridge 400 comprises a top portion 405 (e.g., a cover) and a bottom portion 410 (e.g., a base) in which are mounted at least one microfabricated sensor chip 415 with electrical contacts and a pouch 420 containing a fluid, e.g., a wash fluid. The at least one sensor chip 415 may be positioned in recessed region 418 and configured to generate electric signals based on a concentration of specific chemical species in a fluid sample, e.g., a blood sample from a patient. In some embodiments, the composition of the fluid in the pouch 420 is selected from the group consisting of water, calibrant fluid, reagent fluid, control fluid, wash fluid and combinations thereof. A gasket 425 is situated between the top portion 405 and the bottom portion 410 to bond them together and to define and seal several cavities and conduits within the cartridge 400. The gasket 425 may cover substantially the entire area between the top portion 405 and the bottom portion 410 of the cartridge 400, as shown in FIG. 4, or may be localized over and between only predetermined structural features, e.g., the at least one sensor chip 415, of the cartridge 400 (not shown). The gasket 425 may include apertures 430 to enable physical, fluidic and/or gaseous communication between structural features of the top portion 405 and the bottom portion 410. The gasket 425 may or may not have an adhesive surface, and may have an adhesive surface on both sides thereof, i.e., forming a double-sided adhesive layer.

As shown in FIGS. 5A-5J, in some embodiments, the sensing device or cartridge 500 (e.g., cartridge 400 as described with respect to FIG. 4) has a housing that comprises a top portion 502 (e.g., a cover) and a bottom portion 504 (e.g., a base) formed of rigid and flexible zones of material. As shown in FIGS. 5A-5J, the rigid zones (non-shaded portions) of the cover 502 and the base 504 respectively are preferably each a single contiguous zone; however, the molding process can provide a plurality of non-contiguous substantially rigid zones. The flexible zones (shaded portions) of the cover 502 and the base 504 respectively are preferably a set of several non-contiguous zones. For example, the flexible zone around a displaceable membrane may be separate and distinct from the flexible zone at a closeable sealing member. Alternatively, the flexible zones may comprise a single contiguous zone.

The sensing device or cartridge 500 further comprises a sealable sample entry port 506 and a closable sealing member 508 for closing the sample entry port 502, a sample holding chamber 510 located downstream of the sample entry port 506, a capillary stop 512, a sensor region 514, and a waste chamber 516 located downstream of the sensor region 508. Preferably, the cross-sectional area of a portion of the sample holding chamber 510 decreases distally with respect to the sample entry port 506, as shown by ramp 518 in FIG. 5H. A pouch (e.g., the pouch 420 described with respect to FIG. 4) may be disposed in a recessed region 520 and in fluid communication with a conduit 522 leading to the sensor region 514, optionally via conduit 524. The pouch may be of the design described in U.S. Pat. No. 5,096,669 or, more preferably, in U.S. Pat. No. 8,216,529, both of which are incorporated herein by reference in their entireties. Recessed region 520 preferably includes a spike 525 configured to rupture the pouch, upon application of a force upon the pouch, for example, by reader or analyzer (e.g., analyzer 305 as described with respect to FIG. 3). Once the pouch is ruptured, the system is configured to deliver the fluid contents from the pouch into conduit 522. Movement of the fluid into the conduit 522 and to the sensor region 514 and/or within the conduit 524 may be effected by a pump, e.g., a pneumatic pump connected to the conduit(s) 522 or 524. Preferably, the pneumatic pump comprises a displaceable membrane 526 formed by a portion of a flexible zone 527 of the housing formed over a recessed region or air-bladder 528. In the embodiment shown in FIGS. 5A-5J, upon repeatedly depressing the displaceable membrane 526, the device pumps via conduits 524, 529, 530, and 531 causing fluid from ruptured pouch 206 to flow through the conduit 270, into the conduit 275 and over the sensor region 230.

The closable sealing member 508, in some embodiments, includes a portion of the rigid zone that forms a sealing member 532, and a portion of the flexible zone that forms a seal 533. The sealing member 508 can rotate about hinge 534 and engage the seal 533 with the sample entry port 506 when in a closed position, thus providing an air-tight seal. Alternatively, an air-tight seal may be formed by contact of two flexible materials, e.g., a thermoplastic elastomer (TPE)

on TPE. Optionally, the sealable sample entry port 506 also includes a vent hole (not shown). In an alternative embodiment, a portion of the rigid zone forms a sealing member, and a portion of the flexible zone forms a perimeter seal around the sample entry port, whereby the sealing member can rotate about a hinge and engage the perimeter seal when in a closed position, thus providing an air-tight seal. Alternatively, the perimeter seal may be formed by contact of two flexible materials. In yet another embodiment, the sealing member may include a slidable closure element as described in pending U.S. Pat. No. 7,682,833, the entirety of which is incorporated herein by reference.

The sensor recess 514, in some embodiments, contains a sensor array comprising one or more sensors for one or more different analytes (or blood tests). For example, the sensor array may include an immunosensor and/or a magnetic immunosensor for one or more different analytes (or blood tests). The immunosensor may include a base sensor or sensing electrode on a substantially planar chip (e.g., a microfabricated sensor chip such as the at least one sensor chip 415 described with respect to FIG. 4) where the sensing electrode is positioned in conduit 524 for receiving a sample mixed with a reagent. The magnetic immunosensor may include a base sensor or sensing electrode on a substantially planar chip (preferably the same sensor chip that includes the immunosensor) where the sensing electrode is positioned in the conduit 524 for receiving a sample mixed with reagent that includes beads that can be attracted to a magnet, or respond to a magnetic field that is positioned near the magnetic immunosensor. In alternative embodiments, the sensor array comprises a plurality of sensors for a plurality of different analytes (or blood tests). Accordingly, the cartridge 500 may have one or more sensor recesses 514 each with at least one sensor.

The analytes/properties to which the sensors respond may be selected from among pH, $pCO_2$, $pO_2$, glucose, lactate, creatinine, urea, sodium, potassium, chloride, calcium, magnesium, phosphate, hematocrit, prothrombin time (PT), activated partial thromboblastin time (APTT), activated clotting time (ACT), D-dimer, prostate-specific antigen (PSA), creatine kinase-MB (CKMB), brain natriuretic peptide (BNP), troponin I (TnI), cardiac traponin (cTnI), human chorionic gonadotrophin, troponin T, troponin C, myoglobin, and the like, and combinations thereof. Preferably, the analyte is tested in a liquid sample that is whole blood, however other samples can be used including blood, serum, plasma, urine, cerebrospinal fluid, saliva and amended forms thereof. Amendments can include dilution, concentration, addition of regents such as anticoagulants and the like. Whatever the sample type, it can be accommodated by the sample entry port 502 of the cartridge 500.

The cartridge 500 may further comprise a portion of the flexible zone 536 positioned over the recessed region 520 that is configured for being actuated upon like a pump to apply pressure within the recessed region 520. In some embodiments, the flexible zone 536 may include a generic symbol description to indicate to the user that pressure should not be applied to the flexible zone 536 by the user. For example, the symbol may comprise an embossed circle with a crossbar. The portion of the flexible zone 536 provides a surface that can accommodate an actuator feature of the analyzer (e.g., analyzer 305 as described with respect to FIG. 3) to apply a force and burst the underlying pouch in the recessed region 520. The thickness of the plastic in the flexible zone 536 may be preferably from about 200 to about 800 μm, for example about 400 μm. Essentially, the flexible zone 536 should be sufficiently thin to flex easily, but sufficiently thick to maintain physical integrity and not tear.

Sensor and Chip Designs

In one embodiment, a microfabricated sensor chip (e.g., the at least one sensor chip 415 described with respect to FIG. 4) comprises at least one sensor or transducer (e.g., a working electrode or optical detector). For example, the microfabricated sensor chip may comprise a pair of sensors comprising a first sensor (e.g., a low-end sensitivity sensor) and optionally a second sensor (e.g., a high-end sensitivity sensor). In some embodiments, the sensors may be fabricated as adjacent structures, respectively, on a silicon chip.

Figure 6A:
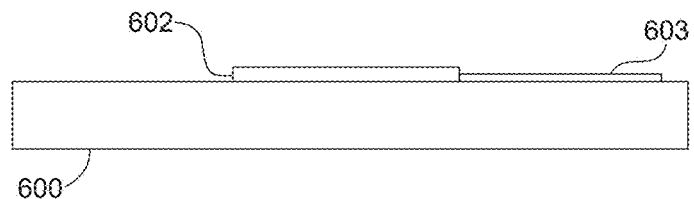
FIG. 6A shows a side view of the fabrication of a sensor chip in accordance with some aspects of the invention.

In various embodiments, the sensors may be formed as electrodes with gold surfaces coated with a photo defined polyimide layer that includes openings to define a grid of small gold electrodes (e.g., a gold microarray electrode) at which an electroactive species may be oxidized. For example, wafer-level micro-fabrication of a preferred embodiment of the sensor chip may be achieved as shown in FIG. 6A. A non-conducting substrate 600 having a planar top and bottom surface may be used as a base for the sensor chip. A conducting layer 602 may be deposited on the substrate 600 by conventional means, e.g., conductive printing, or micro-fabrication technique known to those of skill in the art to form at least one transistor. The conducting layer 602 may comprise a noble metal such as gold, platinum, silver, palladium, iridium, or alloys thereof, although other unreactive metals such as titanium and tungsten or alloys thereof may also be used, as many non-metallic electrodes of graphite, conductive polymer, or other materials may also be used. The microfabricated sensor chip may also comprise an electrical connection 603 that connects the electrode to a conductive pin such as a temporary electrical connector.

In some embodiments, the sensors may comprise an array of 5-10 μm noble metal disks, e.g., 7 μm noble metal disks, on 15 μm centers. The array of noble metal disks or electrodes may cover a region, e.g., a circular region, approximately 300 to 900 μm in diameter, optionally 400-800 μm or about 600 μm in diameter, and may be formed by photo-patterning a thin layer of polyimide or photoresist of thickness up to 1.5 μm over a substrate made from a series of layers comprising Si, $SiO_2$, TiW, and/or Au, or combinations thereof. In some embodiments, the electrodes have a working area of about 130,000 to 300,000 sq μm (i.e., a microelectrode), the volume of sample directly over the electrodes may be about 0.1-0.3 and the volume of the sample over the sensor chip may be 1-3 μL. In accordance with these aspects of the present invention, the conduit (e.g., the conduit 524 described with respect to FIG. 5A) in a region of the electrodes (e.g., the one or more sensor recesses 514 described with respect to FIGS. 5A-5J) has a volume to sensor area ratio of less than about 6 μL to about 1 square mm, preferably less than about 50 mm to about 2 square mm, more preferably less than about 100 μm to about 500 square μm. Accordingly, the array of electrodes affords high collection efficiency of a detectable moiety that is an electroactive species with a reduced contribution from any electrochemical background current associated with the capacitance of the exposed metal. In particular, openings in the insulating polyimide or photoresist layer define a region of the noble metal electrodes at which the electroactive species, e.g., 4-aminophenol, may be oxidized such as in a two electron per molecule reaction.

Micro-fabrication techniques (e.g., photolithography and plasma deposition) may be utilized for construction of the multilayered sensor structures in confined spaces. For example, methods for micro-fabrication of electrochemical immunosensors on silicon substrates are disclosed in U.S. Pat. No. 5,200,051, which is hereby incorporated by reference in its entirety, and include, for example, dispensing methods, methods for attaching substrates and reagents to surfaces including photoformed layers, and methods for performing electrochemical assays.

Figure 6B:
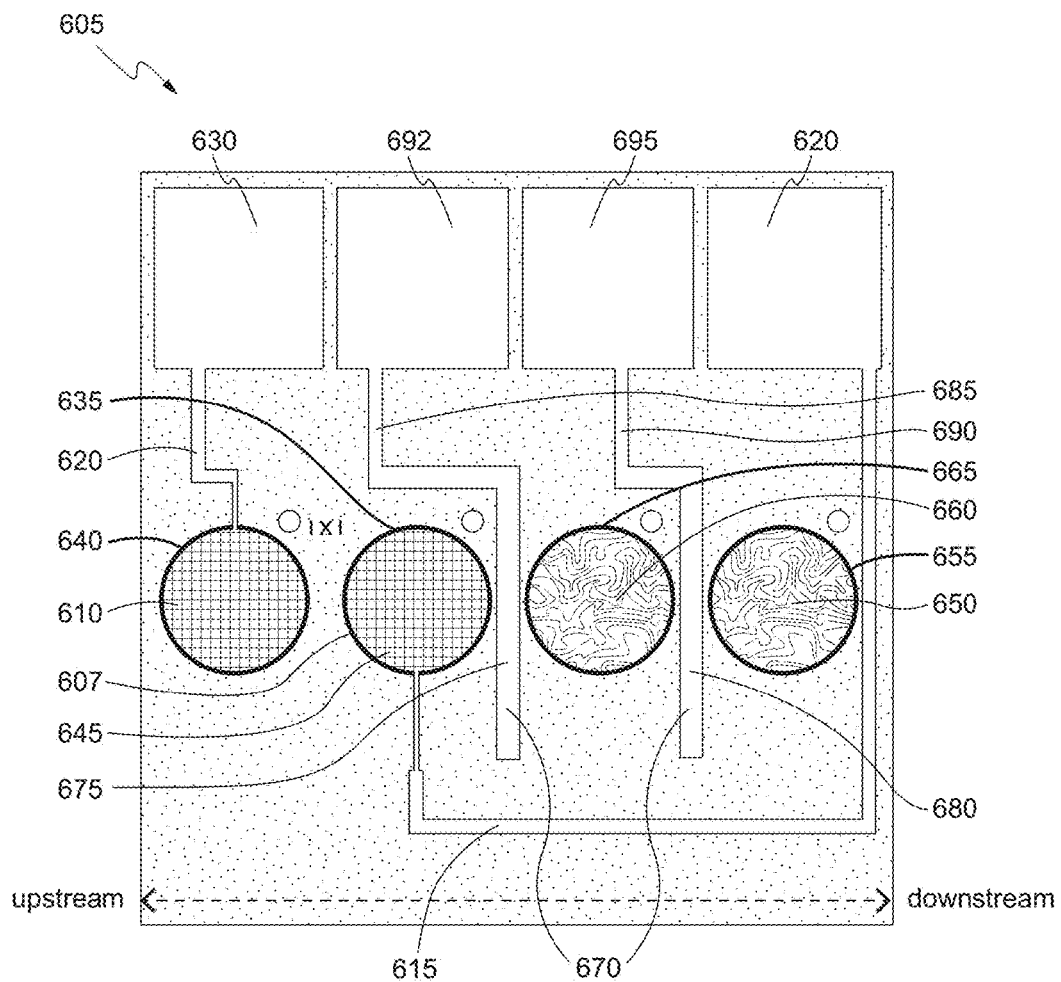
FIGS. 6B, 7, 8A, and 8B show sensor chip configurations in accordance with some aspects of the invention.

As shown in FIG. 6B, in some embodiments, a microfabricated extended range sensor chip 604 includes a first sensor 605 (e.g., a low-end sensitivity amperometric sensor) and optionally a second sensor 610 (e.g., a high-end sensitivity amperometric sensor). The first and second sensors 605, 610 may be fabricated as adjacent structures, respectively, on sensor chip 604. However, in order for the sensor chip 604 to determine accurate analyte concentrations, the low-end sensitivity sensor 605 may be sufficiently spaced from the high-end sensitivity sensor 610. For example, at low to medium concentrations of analyte, the high-end sensitivity sensor 610 may generate a high amperometric signal due to the high concentration of label reagent being attached to antibody coated magnetic beads. In embodiments in which the label reagent uses an enzyme to cleave a substrate generating an electroactive species, the high concentration of the electroactive species at the high-end sensitivity sensor 610 can move along the sensor chip 604 and generate an amperometric signal on the low-end sensitivity sensor 605. Alternatively, the low concentration of the electroactive species at the low-end sensitivity sensor could also move along the sensor chip and generate an amperometric signal on the high-end sensitivity sensor. The magnitude of this crosstalk between the sensors depends on many factors and can display variability between sensing device runs causing increased imprecision on the amperometric reading of the low-end sensitivity sensor and/or the high-end sensitivity sensor. Accordingly, to reduce the crosstalk between sensors it may be beneficial in certain embodiments to space the two sensors from one another by a predetermined distance.

The first sensor 605 and the second sensor 610 are spaced apart from one another at a predetermined distance "x". For example, the first sensor 605 may be spaced at least 0.03 mm, preferably at least 0.06 mm from the second sensor 610. The first sensor 605 may be connected via wiring 615 to a first conductive pin 620 (e.g., temporary electrical connector) and the second sensor 610 may be connected via wiring 625 to a second conductive pin 630 (e.g., temporary electrical connector). In some embodiments, the first sensor 605 may be configured as an immunosensor (e.g., a low-end sensitivity amperometric sensor) and the second sensor 610 may be configured as a magnetic immunosensor (e.g., a high-end sensitivity amperometric sensor) both of which are formed on the single sensor chip 604 and positioned within one or more conduits of the point of care test cartridge. Although it is shown in FIG. 6B that the second sensor 610 is placed upstream from the first sensor 605, it should be understood that alternative embodiments of the present invention contemplate having the second sensor 610 placed downstream from the first sensor 605.

As illustrated in FIG. 6B, the first sensor 605 may be constructed with an array of metal disks or electrodes that cover a circular region in a first area of the sensor chip 604 and the second sensor 610 may be constructed with an array of metal disks or electrodes that cover a circular region in a second area of the sensor chip 604. The design and arrangement of the first and second sensors 605 and 610 on the sensor chip 604 are preferably selected based on printing and performance characteristics (e.g., minimize cross-talk between the sensors) for each of the first and second sensors 605 and 610. However, it should be understood to those of ordinary skill in the art that any design or arrangement for the sensors is contemplated without departing from the spirit and scope of the present invention. Furthermore, although the first and second sensors 605 and 610 in the example in FIG. 6B are described herein as amperometric sensors, other electrochemical processes or optical processes which use other electrochemical or optical sensors, e.g., optical wave guides and charge-coupled device (CCD) camera chips, can be used. For example, a potentiometric sensor may be used to detect ion species such as $Na^+$ or $K^+$.

As described herein, the first and second sensors 605 and 610 may be formed as electrodes with gold surfaces that are exposed (e.g., no polyimide or photoresist covering) to the inside environment of the conduit and configured to directly contact a biological sample disposed within the conduit. The wirings 615 and 620 may be formed with gold surfaces that are coated with a photo defined polyimide or photoresist layer such that the wirings 615 and 620 are insulated from exposure to the biological sample disposed within the conduit. The wirings 615 and 620 may be formed comprising containment ring structures 635 and 640. In some embodiments, the containment ring structure 635 for the first sensor 605 may be configured to contain capture antibodies immobilized on or near the surface of the electrodes. For example, the capture antibodies (as discussed herein) may be deposited onto at least a portion of the first sensor 605 within the containment ring structure 635. The wirings 615 and 620 terminate at the first conductive pin 620 and the second conductive pin 630 respectively, which are used to make contact with a connector in an analyzer or cartridge reader (e.g., an i-STAT® cartridge reader as described in U.S. Pat. No. 4,954,087, the entirety of which is incorporated herein by reference).

In various embodiments, the first sensor 605 is an immunosensor positioned in the conduit for receiving a biological sample mixed with an antibody-enzyme conjugate that is configured to bind to a target analyte within the biological sample. The first sensor 605 may be configured to detect an enzymatically produced electroactive species (e.g., 4-aminophenol) from the reaction of a substrate (e.g., 4-aminophenylphosphate) with the antibody-enzyme conjugate (e.g., one or more antibodies bound to alkaline phosphatase (ALP)). In accordance with these aspects, the first sensor 605 contains a capture region or regions coated with capture antibodies 645 that are configured to bind to a target analyte bound to an antibody-enzyme conjugate. The capture region 645 may be defined by the containment ring structure 635. In some embodiments, the containment ring structure 635 is a hydrophobic ring of polyimide or another photolithographically produced layer. A microdroplet or several microdroplets (approximately 5-40 nL in size) containing capture antibodies in some form, for example bound to beads or microspheres, may be dispensed on the surface of the first sensor 605. The photodefined ring structure 635 contains this aqueous droplet allowing the capture region 645 to be localized to a precision of a few microns. The capture region 645 can be made from 0.03 to roughly 2 $mm^2$ in size. The upper end of this size is limited by the size of the conduit and sensor chip 604 in present embodiments, and is not a limitation of the invention.

In some embodiments, a portion of the sensor chip 604 (e.g., a top surface of the substrate), a wall of the conduit (e.g., the conduit 524 described with respect to FIG. 5A), and/or a wall of the sample chamber (e.g., the sample chamber 510 described with respect to FIGS. 5G and 5H) can be coated with one or more dry reagents to amend the biological sample. For example, the sensor chip 604 may include a reagent region 650 coated with an antibody-enzyme conjugate for an analyte of interest. The reagent region 650 may be defined by a containment ring structure 655. In some embodiments, the containment ring structure 655 is a hydrophobic ring of polyimide or another photo-lithographically produced layer. A microdroplet or several microdroplets (approximately 5-40 nL in size) or a series of about a 100 nanodroplets (approximately 50 to 1000 pL in size) containing the antibody-enzyme conjugate in some form may be dispensed or printed on the surface of the sensor chip 604. The photodefined ring structure 655 contains this aqueous droplet allowing the reagent region 650 to be localized to a precision of a few microns. The reagent region 650 can be made from 0.03 to roughly 2 $mm^2$ in size. The upper end of this size is limited by the size of the conduit and sensor chip 604 in present embodiments, and is not a limitation of the invention.

The biological sample or a fluid may be passed at least once over the dry reagent, e.g., the reagent region 650 to dissolve the reagent within the biological sample or fluid. Reagents used to amend biological samples or fluid within the cartridge may include the antibody-enzyme conjugate, magnetic beads coated with capture antibodies, or blocking agents that prevent either specific or non-specific binding reactions among assay compounds. Within a segment of the biological sample or fluid, the reagent can be preferentially dissolved and concentrated within a predetermined region of the segment. This is achieved through control of the position and movement of the segment. Thus, for example, if only a portion of a segment, such as the leading edge, is reciprocated over the reagent, then a high local concentration of the reagent can be achieved close to the leading edge. Alternatively, if a homogenous distribution of the reagent is desired, for example if a known concentration of a reagent is required for a quantitative analysis, then further reciprocation of the sample or fluid will result in mixing and an even distribution.

In the preferred embodiments of the present invention, the analyzer applies a potential via the first conductive pin 620 to the first sensor 605 and a reference electrode, and measures current changes generated by oxidation current from the substrate as an electrochemical signal. The electrochemical signal being proportional to the concentration of the analyte in the biological sample. The first sensor 605 has an applied potential of approximately +0 mV to 90 mV, e.g., +60 mV versus the reference electrode and, in another preferred embodiment, the first sensor 605 has an applied potential of approximately +40 mV versus the reference electrode. The signal generated by the enzyme reaction product at approximately +10 mV is distinguishable from the signal generated by the unreacted substrate at approximately +200 mV. It should be noted that the exact voltages used to amperometrically detect the substrate and the analyte will vary depending on the chemical structure of the substrate. It is important that the difference in the voltages used to detect the substrate be great enough to prevent interference between the readings.

In various embodiments, the second sensor 610 is a magnetic immunosensor positioned in the conduit for receiving a biological sample mixed with beads that can be attracted to a magnet, or respond to a magnetic field. The beads are coated with capture antibodies that are configured to bind to the target analyte bound to the antibody-enzyme conjugate, e.g., the antibody-enzyme conjugate disposed in reagent region 650 and subsequently dissolved in the biological sample. The second sensor 610 may be configured to detect an enzymatically produced electroactive species (e.g., 4-aminophenol) from the reaction of a substrate (e.g., 4-aminophenylphosphate) with the antibody-enzyme conjugate (e.g., one or more antibodies bound to alkaline phosphatase (ALP)). In accordance with these aspects, a high-field magnet, e.g., a permanent magnet or an electromagnet, may be positioned proximate to the sensor chip 604 (e.g., below) or incorporated into the sensor chip 604, to generate a magnetic field for attracting the beads mixed with the biological sample in the conduit to a location substantially proximate to the second sensor 610. The magnetic field is localized around the second sensor 610 based on the predetermined distance "x" between the first sensor 605 and the second sensor 610, and functions to substantially retain the beads at or near the surface of the second sensor 610 during removal of unbound sample and washing of the electrodes.

The high-field magnet of the present invention may include any material that provides a high magnetic field (e.g., greater than about 0.1 Tesla, greater than 0.4 Tesla or greater than 1 Tesla). The magnetic field can be measured, for example, as a remnant field on a substantially flat surface area of the magnet. In some embodiments, the high-field magnet is comprised of a material such as neodymium iron boron alloy (NdFeB) alloy (e.g., $Nd_2Fe_{14}B$), or ferrite or aluminum nickel cobalt (AlNiCo), which typically exhibit fields of greater than 0.1 Tesla, e.g., greater than 0.5 Tesla or from 0.1 to 1 Tesla. In other embodiments, the high-field magnet is comprised of alloys of rare earth elements (e.g., neodymium alloys and samarium cobalt (SmCo) alloys), which exhibit fields of greater than 0.1 Tesla, e.g., greater than 1.2 Tesla or greater than 1.4 Tesla. In alternative embodiments, the high-field magnet comprises an electromagnet in which the magnetic field is produced by the flow of electric current. The electric current may be provided by an analyzer, in which the sensing device is inserted and with which the sensing device is in electrical contact.

The high-field magnet can be provided proximate to the sensor chip 604 (e.g., below) or incorporated into the sensor chip 604 using a number of techniques as described in detail herein. In some embodiments, the second sensor 610 comprises a sensing electrode on a substantially planar substrate and a bulk permanent high-field magnet positioned proximate to the electrode (e.g., below or on the opposite side of the sensor chip 604). In certain preferred embodiments, the bulk permanent high-field magnet is positioned in the housing (e.g., cut out or trench in the rigid zone of the cartridge) of the sensing device. For example, the bulk permanent high-field magnet may be positioned within the base of the cartridge housing (e.g., non-coplanar with the sensor chip). In other embodiments, the high-field magnet is positioned adjacent to or within the analyzer, in which the sensing device is inserted. The bulk high-field permanent magnet may be substantially cylindrical, having a diameter in the range of about 0.1 mm to about 5 mm and a length of about 0.1 mm to about 5 mm, and is positioned to yield an "event horizon" (as defined herein) in the conduit suitable for bead capture within a short period of time (e.g., 1-5 minutes). The conduit generally has a height of about 0.2 mm to about 5 mm and a width of about 0.2 mm to about 5 mm, and either a uniform or non-uniform cross-sectional area. Alternatively, the bulk magnet shape may be in the form of a square, rectangle, oval, flake, pyramid, sphere, sub-sphere, or other shaped form.

In alternative embodiments, the second sensor 610 comprises a sensing electrode on a substantially planar substrate and a magnetized layer (e.g., microfabricated magnetic layer). The magnetized layer may be included on (e.g., positioned over, directly attached, coated or patterned onto any surface of the sensor chip 604) or embedded into the chip (e.g., positioned within the chip, integral to the chip). This configuration attracts the magnetically susceptible beads substantially proximate to or on the sensing electrode and substantially retains them at the sensing electrode during removal of unbound sample and washing of the sensing electrode.

The magnetized layer may be a composite material formed from a particulate magnetic material capable of sustaining a high-field permanent magnetic field, e.g., a NdFeB alloy, in a binder or support matrix (e.g., a thermal setting ink, a polyimide, polyvinyl alcohol (PVA) or thermoplastic equivalent). In addition to thermal setting ink, polyimide, PVA and thermoplastic equivalents, two-part chemically cured epoxy resins, kapton and the like may be used as the binder for fixing the particulate magnetic material to the sensor chip. In some embodiments, the binder is comprised of a thermal setting ink such as a solvent based encapsulant screen printing ink or an acrylic acid polymer in a solvent. In alternative embodiments, the binder is comprised of other photoformed matrix materials. The methods of curing the composite material may be based on a photo-initiated, thermally initiated or a chemically initiated process. The composite material is not limited by viscosity and can include any viscosity suitable for application. In some embodiments, the composite material has a viscosity ranging from 0.3 to 300,000 CPS, e.g., from 100 to 100,000 CPS or from 1,000 to 10,000 CPS. The magnetic particles in the composite material of certain embodiments have an average particle size from 0.01 µm to 100 µm, e.g., from 0.1 µm to 10 µm or from 3 µm to 7 µm.

The composite material can be applied in a variety of locations in or on the sensing device (e.g., to the front side or backside of a wafer or chip, electrode, housing, reader, etc.). For example, in some embodiments, the composite material is applied to the sensor chip in a patterned manner (e.g., using a mask). In other embodiments, the composite material is applied to the sensing electrode. In other embodiments, the composite material is applied in a magnetized layer below the sensing electrode. Prior to the application of the magnetized layer, the magnetized layer may or may not be magnetized. However, after the application, the magnetic layer preferably is magnetized to provide directionality to the magnetic field generated by the magnetized layer.

In some embodiments, a portion of the sensor chip 604 (e.g., a top surface of the substrate), a wall of the conduit (e.g., the conduit 524 described with respect to FIG. 5A), and/or a wall of the sample chamber (e.g., the sample chamber 510 described with respect to FIGS. 5G and 5H) can be coated with one or more dry reagents to amend the biological sample. For example, the sensor chip 604 may include a reagent region 660 coated with magnetic beads having capture antibodies for an analyte of interest. The reagent region 660 may be defined by a containment ring structure 665. In some embodiments, the containment ring structure 665 is a hydrophobic ring of polyimide or another photolithographically produced layer. A microdroplet or several microdroplets (approximately 5-40 nL in size) containing the antibody-enzyme conjugate in some form may be dispensed or printed on the surface of the sensor chip 604. The photodefined ring structure 665 contains this aqueous droplet allowing the reagent region 660 to be localized to a precision of a few microns. The reagent region 665 can be made from 0.03 to roughly 2 mm$^2$ in size. The upper end of this size is limited by the size of the conduit and sensor chip 604 in present embodiments, and is not a limitation of the invention. Although it is shown in FIG. 6B that the reagent region 660 is placed upstream from the reagent region 650, it should be understood that alternative embodiments of the present invention contemplate having the reagent region 660 placed downstream from the reagent region 650.

The biological sample or a fluid may be passed at least once over the dry reagent, e.g., the reagent region 660 to dissolve the reagent within the biological sample or fluid. Reagents used to amend biological samples or fluid within the cartridge may include the antibody-enzyme conjugate, magnetic beads coated with capture antibodies, or blocking agents that prevent either specific or non-specific binding reactions among assay compounds. Within a segment of the biological sample or fluid, the reagent can be preferentially dissolved and concentrated within a predetermined region of the segment. This is achieved through control of the position and movement of the segment. Thus, for example, if only a portion of a segment, such as the leading edge, is reciprocated over the reagent, then a high local concentration of the reagent can be achieved close to the leading edge. Alternatively, if a homogenous distribution of the reagent is desired, for example if a known concentration of a reagent is required for a quantitative analysis, then further reciprocation of the sample or fluid will result in mixing and an even distribution.

In the preferred embodiments of the present invention, the analyzer applies a potential via the second conductive pin 630 to the second sensor 610 and a reference electrode, and measures current changes generated by oxidation current from the substrate as an electrochemical signal. The electrochemical signal being proportional to the concentration of the analyte in the biological sample. The second sensor 610 has an applied potential of approximately +0 mV to 90 mV, e.g., 60 mV versus the reference electrode and, in another preferred embodiment, the first sensor 605 has an applied potential of approximately +40 mV versus the reference electrode. The signal generated by the enzyme reaction product at approximately +10 mV is distinguishable from the signal generated by the unreacted substrate at approximately +200 mV. It should be noted that the exact voltages used to amperometrically detect the substrate and the analyte will vary depending on the chemical structure of the substrate. It is important that the difference in the voltages used to detect the substrate be great enough to prevent interference between the readings.

In some embodiments, the sensor chip 604 may further include a conductometric sensor 670 (e.g., hematocrit sensors). The conductometric sensor 670 is configured to determine biological sample arrival and/or departure at the reagent regions 650 and 660 and biological sample arrival and/or departure at the first and second sensors 605 and 610. More specifically, the conductometric sensor 670 lie perpendicular to a length of the conduit or sensor conduit, and an electrical resistance between pairs of electrodes for the sensor may be used to monitor a relative position of a fluid front of the biological sample. At the extremes, an open circuit reading indicates that the biological sample has been pushed off the reagent regions 650 and 660 and a closed circuit reading indicates the reagent regions 650 and 660 are covered with the biological sample.

As shown in FIG. 6B, the conductometric sensor 670 may comprise at least two electrodes 675 and 680 (i.e., electrode pair) positioned downstream of the first and second sensors 605 and 610. The electrodes 675 and 680 may be connected via wirings 685 and 690 to a conductometric low pin 692 and an AC source or conductometric high pin 695, respectively (e.g., temporary electrical connectors). The wirings 685 and 690 may be formed with a gold surface that is coated with a photo defined polyimide or photoresist layer such that the wirings 685 and 690 are insulated from exposure to the biological sample disposed within the conduits. As such, in some embodiments, the biological sample or fluid reaches the electrode pair in a conduit (e.g., prior to arriving at the first and second sensors 605 and 610), then subsequently arrives at the first and second sensors 605 and 610 (e.g., after departing the reagent regions 650 and 660).

Figure 7:
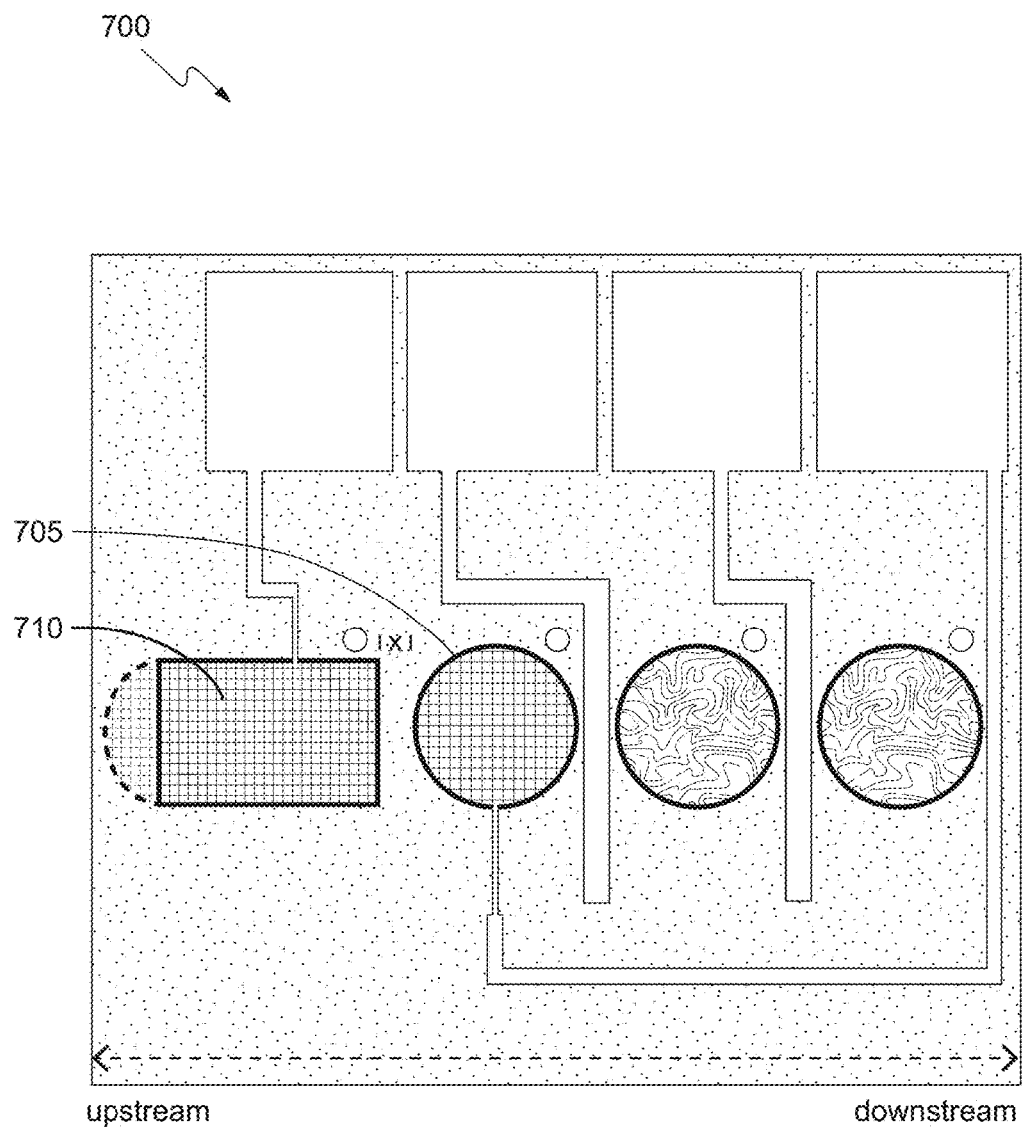

As shown in FIG. 7, in alternative embodiments, a microfabricated sensor chip 700 includes a first sensor 705 (e.g., a low-end sensitivity amperometric sensor) and optionally a second sensor 710 (e.g., a high-end sensitivity amperometric sensor), as similarly described with respect to FIG. 6B. However, as illustrated in FIG. 7, the first sensor 705 may be constructed with an array of metal disks or electrodes that cover a circular region in a first area of the sensor chip 700 and the second sensor 710 may be constructed with an array of metal disks or electrodes that cover a square or elongated region 715 in a second area of the sensor chip 700. The square or elongated region 715 in a second area of the sensor chip 700 provides a larger surface area for the magnet or magnetic field to capture the beads coated with capture antibodies dispersed with the biological sample, as the biological sample passes through the conduit over the sensors. As should be understood, the microfabricated sensor chip 700 may include one or more of the same additional features such as the reagent regions and the conductometric sensor as described with respect to the sensor chip 604 and FIG. 6B.

Figure 8A:
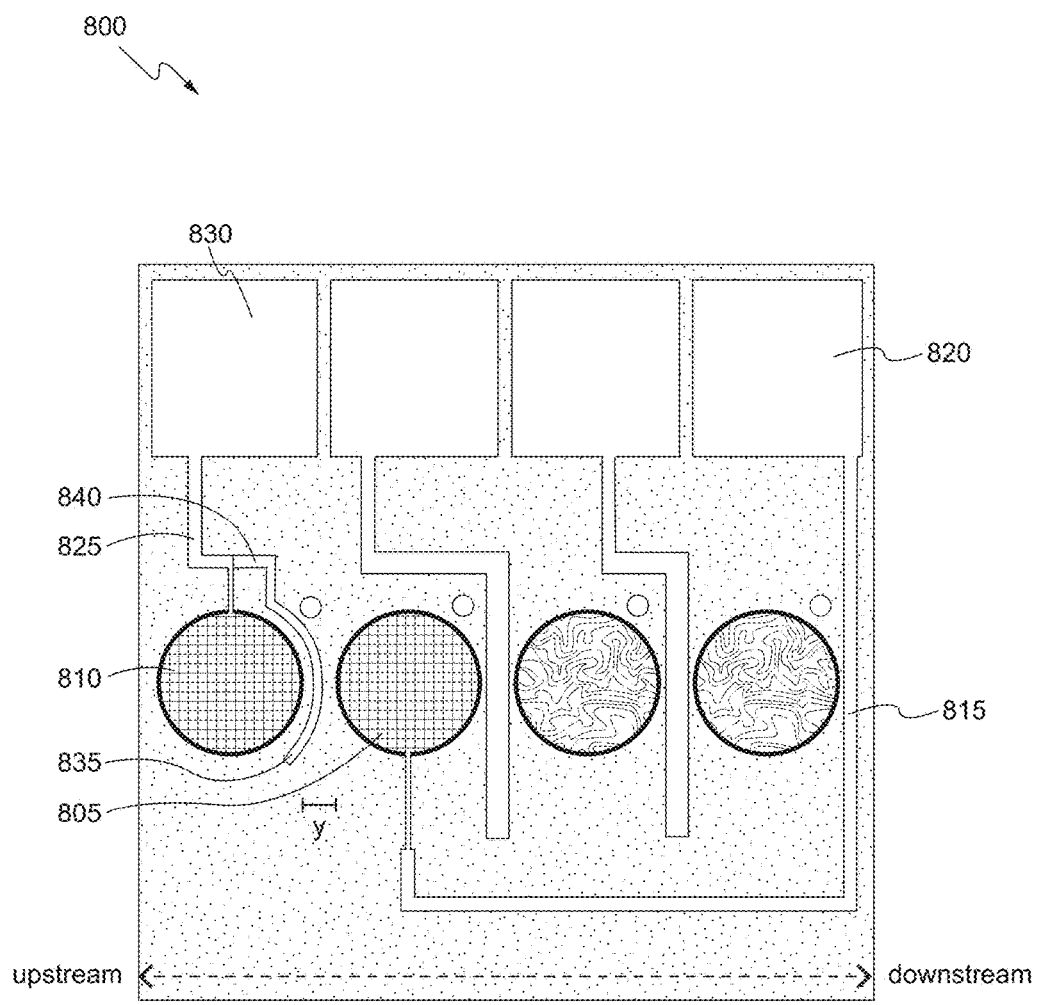
Figure 8B:
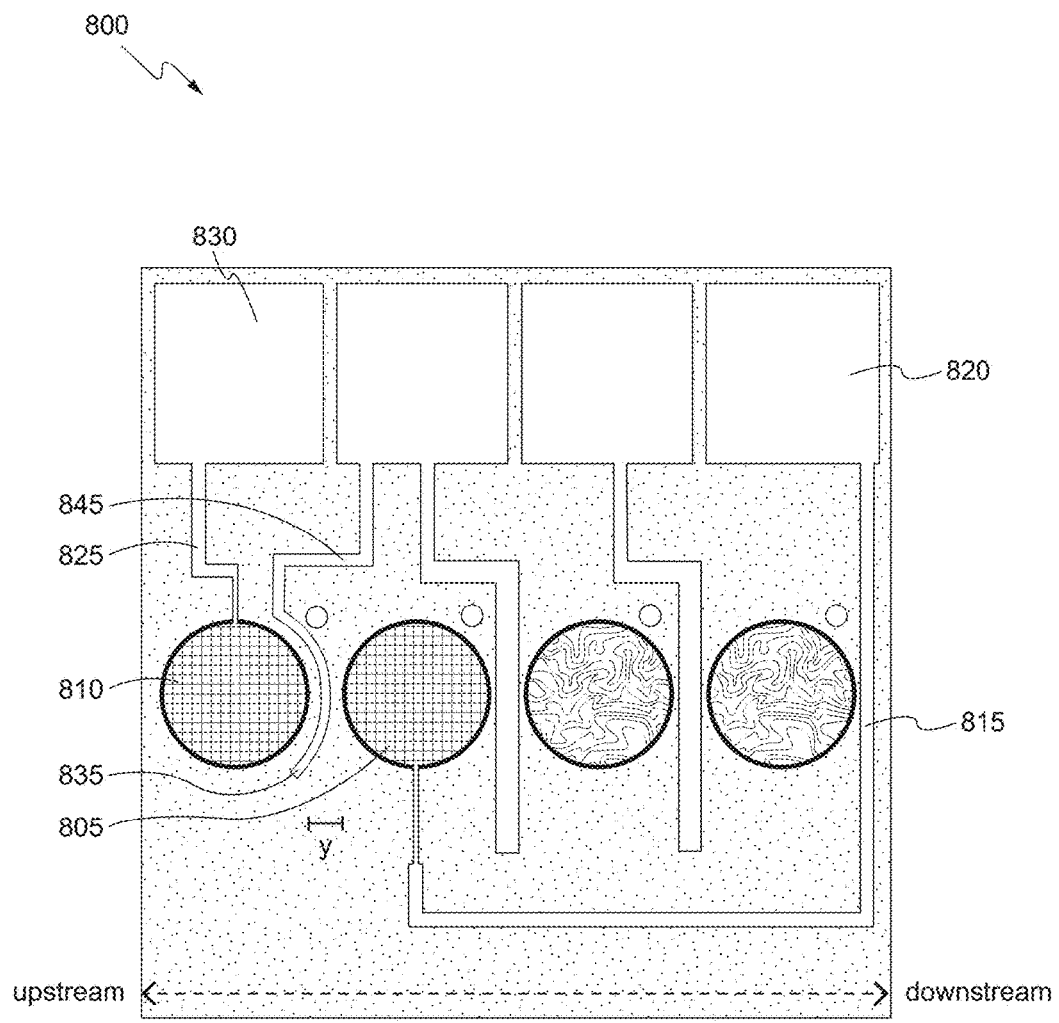

As shown in FIGS. 8A and 8B, in other embodiments designed to lower the crosstalk between the two sensors, a microfabricated extended range sensor chip 800 (e.g., the at least one sensor chip 415 described with respect to FIG. 4) is provided for that comprises a pair of sensors comprising a first sensor (e.g., a low-end sensitivity sensor) and a second sensor (e.g., a high-end sensitivity sensor) with a scavenging electrode provided between the sensors. In some embodiments, the first and second sensors may be fabricated as adjacent structures, respectively, on a silicon chip. However, in order for the extended range sensor chip to determine accurate analyte concentrations, the low-end sensitivity sensor may be sufficiently isolated from the high-end sensitivity sensor. For example, at low to medium concentrations of analyte, the high-end sensitivity sensor may generate a high amperometric signal due to the high concentration of the label reagent being attached to the antibody coated magnetic beads. In embodiments in which the label reagent uses an enzyme to cleave a substrate generating an electroactive species, the high concentration of the electroactive species at the high-end sensitivity sensor can move along the sensor chip and generate an amperometric signal on the low-end sensitivity sensor. Alternatively, the low concentration of the electroactive species at the low-end sensitivity sensor could also move along the sensor chip and generate an amperometric signal on the high-end sensitivity sensor. The magnitude of this crosstalk between the sensors depends on many factors and can display variability between sensing device runs causing increased imprecision on the amperometric reading of the low-end sensitivity sensor and/or the high-end sensitivity sensor. Accordingly, it may be beneficial in certain circumstances to lower the crosstalk between the two sensors in the extended range sensor chip using a scavenging electrode.

The microfabricated sensor chip 800 includes a first sensor 805 (e.g., a low-end sensitivity amperometric sensor) and a second sensor 810 (e.g., a high-end sensitivity amperometric sensor), as similarly described with respect to FIG. 6B. However, the first sensor 805 and the second sensor 810 are spaced apart from one another at an increased distance "y" as compared to the sensor chip 604 shown in FIG. 6B. For example, the first sensor 805 may be spaced at least 0.2 mm, preferably at least 0.5 mm from the second sensor 810. The first sensor 805 may be connected via wiring 815 to a first conductive pin 820 (e.g., temporary electrical connector) and the second sensor 810 may be connected via wiring 825 to a second conductive pin 830 (e.g., temporary electrical connector). In some embodiments, the first sensor 805 may be configured as an immunosensor (e.g., a low-end sensitivity amperometric sensor) and the second sensor 810 may be configured as a magnetic immunosensor (e.g., a high-end sensitivity amperometric sensor) both of which are formed on the single sensor chip 800 and positioned within one or more conduits of the point of care test cartridge.

As shown in FIGS. 8A and 8B, the increased spacing "y" between the first sensor 805 and the second sensor 810 allows for a scavenging electrode 835 to be positioned between the first sensor 805 and the second sensor 810. Specifically, the design and arrangement of the first and second sensors 805 and 810 on the sensor chip 800 are selected to allow for the addition of the scavenging electrode 835 between the first sensor 805 and the second sensor 810. The scavenging electrode 835 is configured to oxidize the electroactive species generated at the second sensor 810 so that high signals at the second sensor 810 do not result in significant crosstalk at the first sensor 805 and/or low signals at the first sensor 805 do not result in significant crosstalk at the second sensor 810. For example, the scavenging electrode is configured to (i) prevent electroactive species generated in a region of the second sensor from diffusing to the first sensor, (ii) prevent electroactive species generated in a region of the second sensor from being transported to the first sensor, (iii) prevent electroactive species generated in a region of the second sensor from being detected at the first sensor, (iv) prevent electroactive species generated in a region of the first sensor from diffusing to the second sensor, (v) prevent electroactive species generated in a region of the first sensor from being transported to the second sensor, and/or (vi) prevent electroactive species generated in a region of the first sensor from being detected at the second sensor.

In some embodiments, as shown in FIG. 8A, the scavenging electrode 835 is connected via wiring 840 to the second sensor 810. In alternative embodiments, as shown in FIG. 8B, the scavenging electrode 1735 is connected via wiring 845 to a conductometric low pin 850 (e.g., temporary electrical connector for the conductivity sensor). Both configurations of the scavenging electrode 835 are designed to minimize crosstalk while resulting in low impact on the signal generated at the second sensor 810 and the signal generated at the first sensor 805. As should be understood, the microfabricated sensor chip 800 may include one or more of the same additional features such as the reagent regions and the conductometric sensor as described with respect to the sensor chip 604 and FIG. 6B.

Magnetic Immunosensor Configurations

Figure 9A:
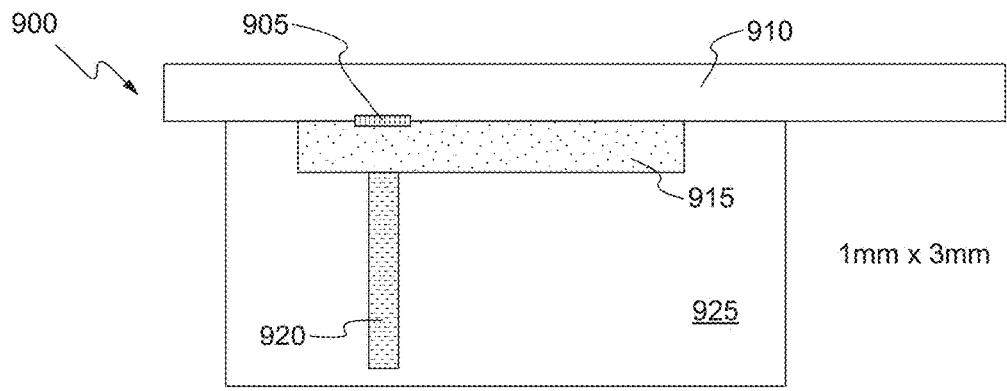
FIGS. 9A-9C illustrate various exemplary configurations for the positioning of a magnet below a sensor chip within a cartridge in accordance with some aspects of the invention.
Figure 9B:
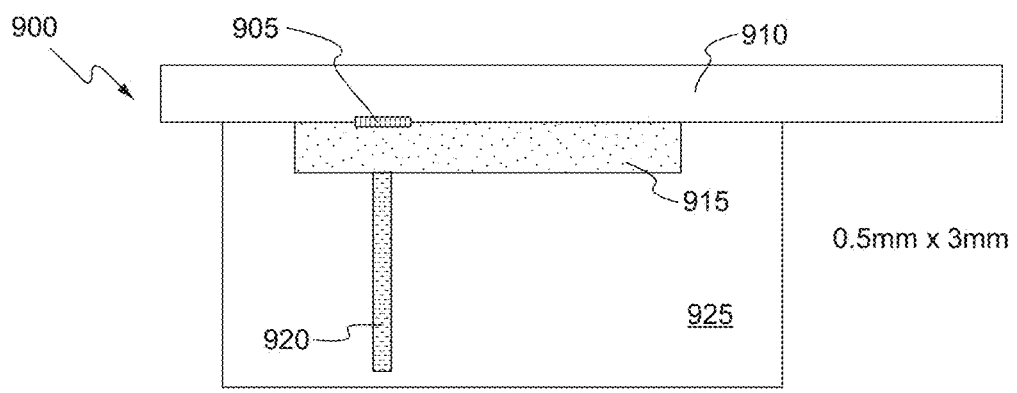
Figure 9C:
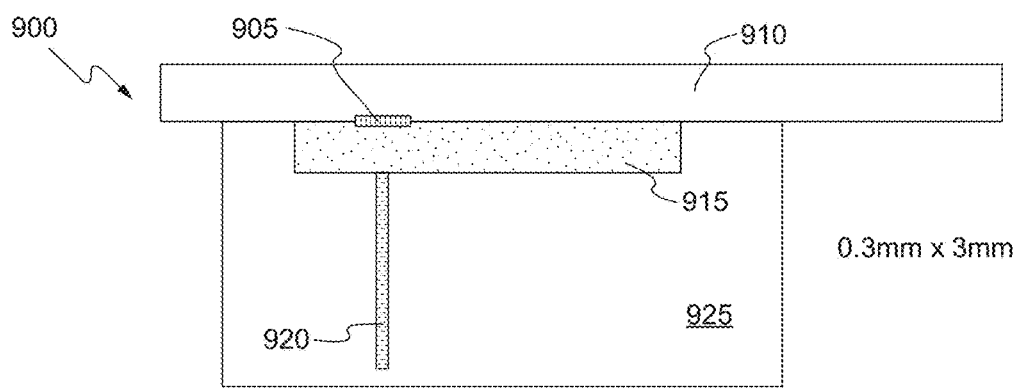

FIGS. 9A-9C show three exemplary embodiments of a magnetic immunosensor (e.g., a high-end sensitivity amperometric sensor 610 as described with respect to FIG. 6B) where the magnetic component is directly integrated into the base or cartridge housing of the sensing device. In each embodiment shown in FIGS. 9A-9C, the sensor chip 900 includes an immunosensor 905 disposed in a conduit 910 and positioned on a surface of a substrate 915 above a high-field magnet 920. The high-field magnet 920 may be cylindrical with a length of from 1 mm to 10 mm, e.g., from 2 mm to 5 mm, preferably about 3 mm, and a diameter of from 0.1 mm to 5 mm, e.g., from 0.5 mm to 2 mm. In FIGS. 9A-9C, the high-field magnet 920 has diameters of about 1 mm, about 0.5 mm and about 0.3 mm, respectively. The high-field magnet 920 is within the base or cartridge housing 925 (e.g., a bottom portion or base 504 as described with respect to FIGS. 5A-5J) of the sensing device and optionally is abutted to the underside of the sensor chip 900, which preferably has a thickness of from about 0.2 mm to 5 mm, e.g., from 0.5 mm to 2 mm or preferably about 1 mm. In accordance with these aspects, a high-field magnet, e.g., a permanent magnet or an electromagnet, may be positioned proximate to the sensor chip 900 (e.g., below), for attracting magnetically susceptible beads in the conduit substantially proximate to or on the sensor 905.

Figure 10:
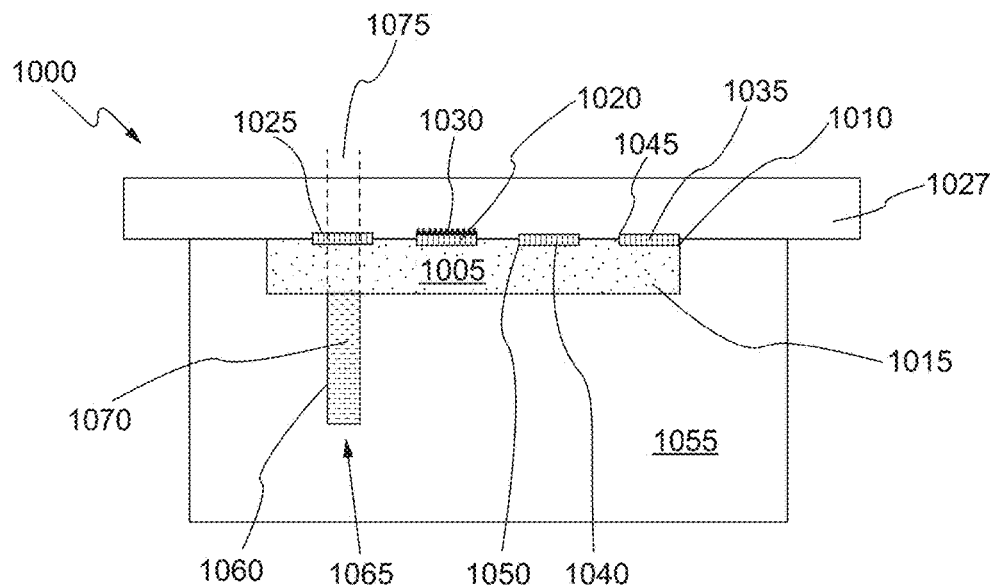
FIG. 10 illustrates an exemplary configuration for the positioning of sensors on a sensor chip within a cartridge in accordance with some aspects of the invention.

As shown in FIG. 10, a device 1000 for detecting an analyte in a biological sample in accordance with the some aspects of the present invention comprises a substrate 1005 including a planar top and bottom surface 1010, 1015, a first electrochemical sensor 1020 (e.g., a low-end sensitivity amperometric sensor) positioned on the top surface 1010 of the substrate 1005, and a second electrochemical sensor 1025 (e.g., a high-end sensitivity amperometric sensor) positioned on the top surface 1010 of the substrate 1005 and adjacent to the first electrochemical sensor 1020. In some embodiments, the substrate 1005 is disposed within a conduit 1027 of the device 1000. The substrate 1005 may be comprised of a base material selected from the group consisting of silicon, glass, and plastic. The first electrochemical sensor 1020 may include an immobilized layer of antibody 1030 configured to bind to an analyte such as cTnI. The first electrochemical sensor 1020 and the second electrochemical sensor 1025 may comprise a gold microarray electrode and have a diameter from about 100 µm to about 500 µm or from about 200 µm to about 1500 µm.

The device 1000 further includes (i) a first reagent region 1035 on the substrate 1005 coated with an antibody-enzyme conjugate for the analyte, and/or (ii) a second reagent region 1040 on the substrate 1005 coated with magnetic beads having capture antibodies for the analyte. The reagent regions 1035, 1040 may be defined by a containment ring structure 1045, 1050, respectively. In other embodiments, the reagent regions 1035, 1040 may be located on the conduit 1027 (e.g., the conduit 524 described with respect to FIG. 5A), and/or in the sample chamber (e.g., the sample chamber 510 described with respect to FIGS. 5G and 5H).

The device 1000 further includes a housing 1055 that supports the substrate 1005. The housing 1055 having an opening or trench 1060 that extends to a region 1065 in the housing below the second electrochemical sensor 1025. The opening or trench 1060 comprises a high-field magnet 1070 (e.g., bulk permanent high-field magnet) that optionally abuts the planar bottom surface 1015 of the substrate 1005. The high-field magnet 1070 has a shape (e.g., a shape that is substantially triangular, trapezoid, column, rectangle, square, circular, pyramid, etc. (substantially in this context would be understood by those of ordinary skill in the art to mean that visually the shape is by and large triangular, trapezoid, column, rectangle, square, circular, pyramid, etc)) that fits within the opening or trench 1060. Moreover, the high-field magnet 1070 generates a magnetic field 1075 that is aligned (e.g., on a same vertical plane) with respect to the second electrochemical sensor 1025 and/or orthogonal to a horizontal plane of the top surface 1010 of the substrate 1005. The magnetic field 1075 is configured to focus and attract the magnetic beads onto a surface of the second electrochemical sensor 1025 once the magnetic beads are mixed with the biological sample.

Figures 11A, 11B:
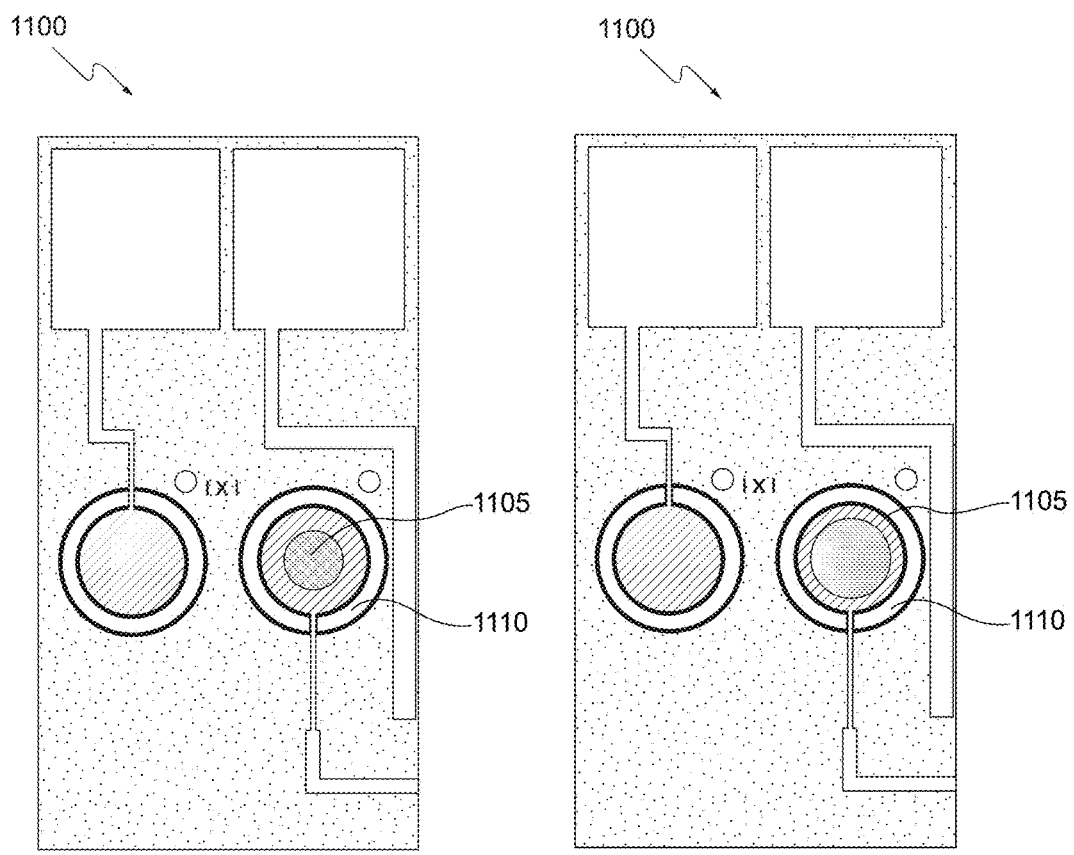
FIGS. 11A and 11B show exemplary immunosensors partially covered with a printed magnetic layer leaving a portion of the perimeter of the immunosensor exposed in accordance with some aspects of the invention.

In alternative embodiments, a magnetic immunosensor (e.g., a high-end sensitivity amperometric sensor 610 as described with respect to FIG. 6B) is provided where the magnetic component is directly integrated into the sensor manufacture, rather than being a separate component (e.g., bulk permanent high-field magnet) requiring assembly into the base or cartridge housing of the sensing device. The magnetized layer may be formed from a composite material, e.g., slurry, comprising a particulate magnetic material capable of sustaining a high-field permanent magnetic field, e.g., a NdFeB alloy, in a binder or support matrix (e.g., a polyimide, polyvinyl alcohol (PVA) or thermoplastic equivalent). In one embodiment, a mixture of photoformable polyvinyl alcohol (PVA) mixed with ground $Nd_2Fe_{14}B$ powder is printed onto a wafer using a microdispensing apparatus of the type described in U.S. Pat. No. 5,554,339, which is incorporated herein by reference in its entirety. The printed area may be a diameter of about 400 µm, or from 200 to 600 µm. FIGS. 11A and 11B show exemplary immunosensors 1100 partially covered with a printed polyimide and NdFeB particle matrix 1105 leaving a portion 1110 of the perimeter of the magnetic immunosensors exposed.

Figure 12:
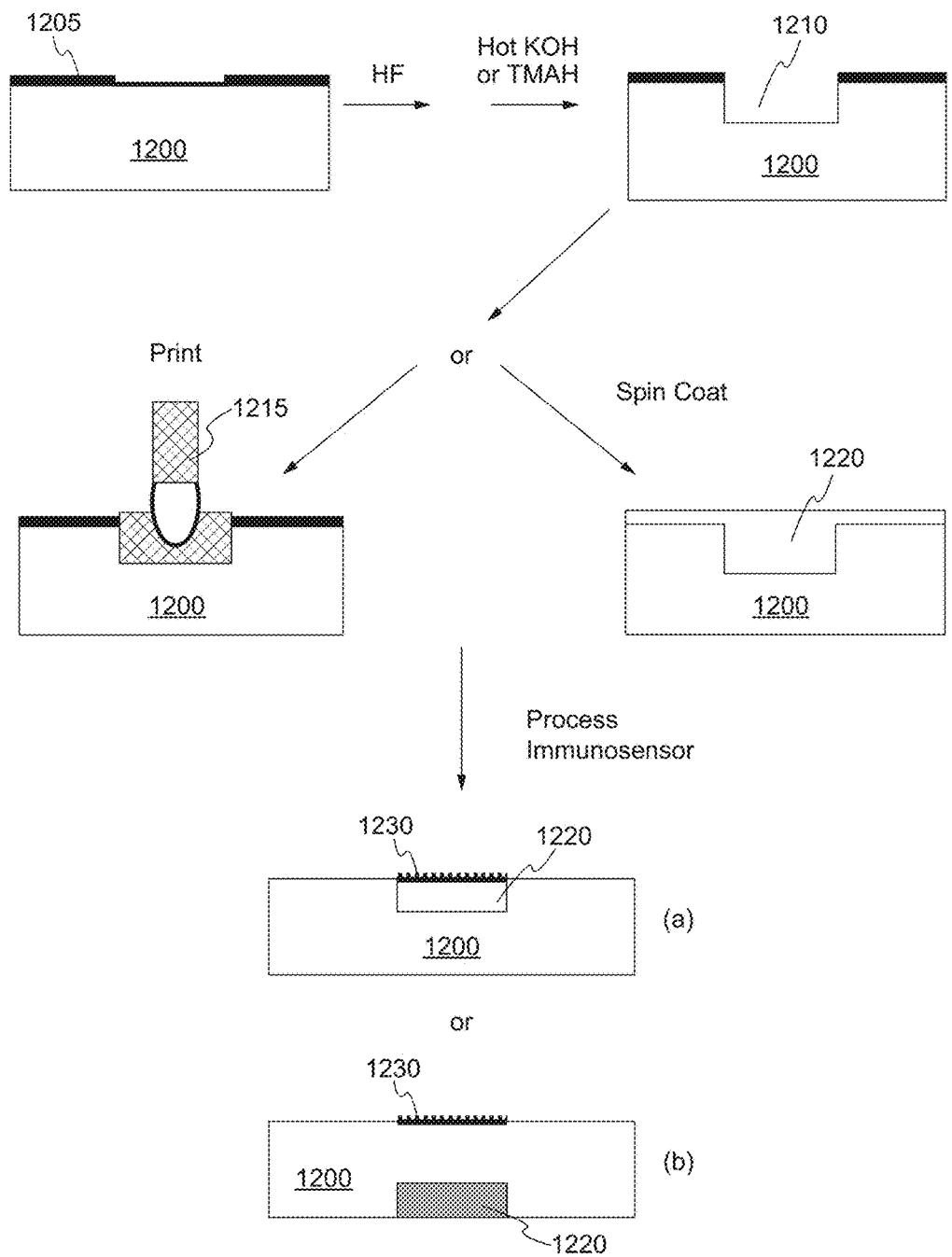
FIG. 12 illustrates an etched trench process in accordance with some aspects of the invention.

In another embodiment, the slurry of magnetizable particles (e.g., ground $Nd_2Fe_{14}B$ powder) is deposited in a trench within the non-conducting substrate or wafer of the microfabricated sensor chip. FIG. 12 illustrates trench forming process that comprises initially etching a non-conducting substrate 1200 (e.g., a silicon wafer) having a surface coating of photoresist 1205 with hydrofluoric acid (HF) and then etching the substrate with hot potassium hydroxide (KOH) or trimethyl ammonium hydroxide (TMAH) to leave a trench 1210 of controlled profile (e.g., a shape that is substantially triangular, trapezoid, column, rectangle, square, circular, pyramid, etc. (substantially in this context would be understood by those of ordinary skill in the art to mean that visually the shape is by and large triangular, trapezoid, column, rectangle, square, circular, pyramid, etc)) and dimensions (e.g., a depth and width of from about 5 µm to about 600 µm). A slurry of magnetizable particles (e.g., NdFeB alloy powder) in a thermoplastic matrix (e.g., polyimide) is then microdispensed 1215 or spin-coated 1220 into the trench 1210 to form a magnetized layer 1225 having a substantially flat surface co-planar with the substrate 1200. The substrate 1200 may be further processed, as described in jointly-owned U.S. Pat. Nos. 7,419,821 and 7,723,099, which are incorporate herein by reference in their entireties, to provide an immunosensor array 1230 over each etched trench 1210 on the substrate 1200. The immunosensor array 1230 may be deposited directly on the magnetized layer 1225 as shown in (a) or over the magnetized layer 1225 as shown in (b).

Figure 13:
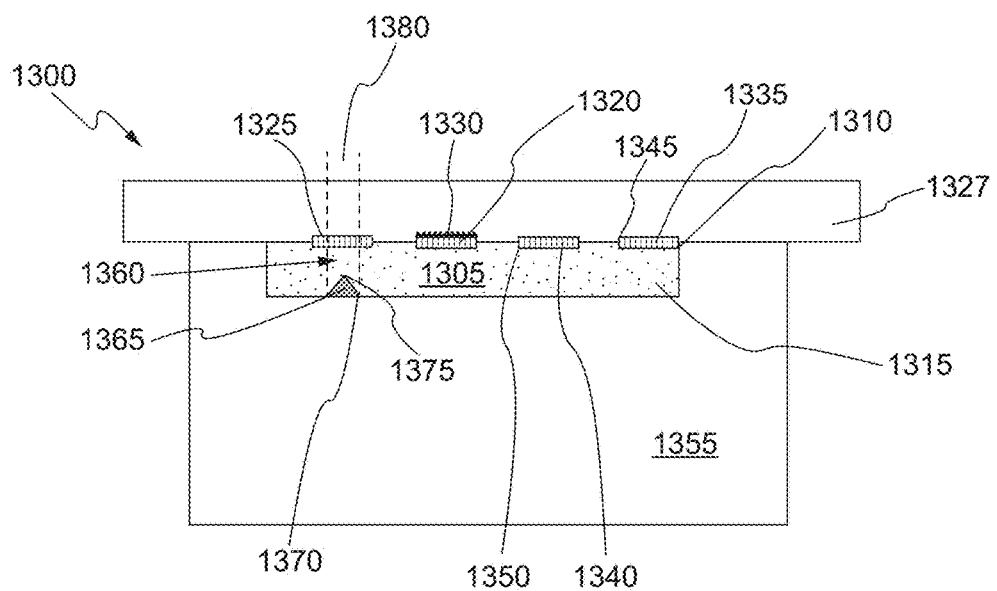
FIG. 13 illustrates an exemplary configuration for the positioning of sensors on a sensor chip within a cartridge in accordance with some aspects of the invention.

As shown in FIG. 13, a device 1300 for detecting an analyte in a biological sample in accordance with the some aspects of the present invention comprises a substrate 1305 including a planar top and bottom surface 1310, 1315, a first electrochemical sensor 1320 (e.g., a low-end sensitivity amperometric sensor) positioned on the top surface 1310 of the substrate 1305, and a second electrochemical sensor 1325 (e.g., a high-end sensitivity amperometric sensor) positioned on the top surface 1310 of the substrate 1305 and adjacent to the first electrochemical sensor 1320. In some embodiments, the substrate 1305 is disposed within a conduit 1327 of the device 1000. The substrate 1305 may be comprised of a base material selected from the group consisting of silicon, glass, and plastic. The first electrochemical sensor 1320 may include an immobilized layer of antibody 1330 configured to bind to an antibody such as cTnI. The first electrochemical sensor 1320 and the second electrochemical sensor 1325 may comprise a gold microarray electrode and have a diameter from about 100 µm to about 500 µm or from about 200 µm to about 1500 µm.

The device 1300 further includes (i) a first reagent region 1335 on the substrate 1305 coated with an antibody-enzyme conjugate for the analyte, and/or (ii) a second reagent region 1340 on the substrate 1005 coated with magnetic beads having capture antibodies for the analyte. The reagent regions 1335, 1340 may be defined by a containment ring structure 1345, 1350, respectively. In other embodiments, the reagent regions 1335, 1340 may be located on the conduit 1327 (e.g., the conduit 524 described with respect to FIG. 5A), and/or in the sample chamber (e.g., the sample chamber 510 described with respect to FIGS. 5G and 5H).

The device 1300 further includes an opening or trench 1355 in the bottom surface 1315 of the substrate extending to a region 1360 in the substrate 1305 below the second electrochemical sensor 1325. The opening or trench 1355 comprises a composite material 1365 including a binder (e.g., the binder is comprised of polyimide or polyvinyl alcohol) and a particulate magnetic material (e.g., the particulate magnetic material is comprised of neodymium iron boron (NdFeB) alloy or aluminum nickel cobalt (AlNiCo) alloy) that optionally fills the opening or trench 1355. The composite material 1365 is configured to take on the shape of the opening or trench 1355 (e.g., a shape that is substantially triangular, trapezoid, column, rectangle, square, circular, pyramid, etc. (substantially in this context would be understood by those of ordinary skill in the art to mean that visually the shape is by and large triangular, trapezoid, column, rectangle, square, circular, pyramid, etc)).

In some embodiments, a shape of the opening or trench 1355 includes a substantially triangular cross-section, a base 1370 of the substantially triangular cross-section is co-planar with the bottom surface 1315 of the substrate 1305, and an apex 1375 of the substantially triangular cross-section is below the second electrochemical sensor 1325. The opening or trench 1355 may have a diameter from about 200 µm to about 1500 for example from 500 µm to 1000 µm. The substantially triangular cross-section shape of the opening may be selected from the group consisting of: a cone, a pyramid, a tetrahedron, a polygon of conical form, and a V-shaped trench. The substantially triangular cross-section may extend through at least 75%, 90%, or 95% of a distance from the bottom surface 1315 to the top surface 1310 of the substrate 1305. The composite material 1365 generates a magnetic field 1380 that is aligned (e.g., on a same vertical plane) with respect to the second electrochemical sensor 1325 and/or orthogonal to a horizontal plane of the top surface 1310 of the substrate 1305. The magnetic field 1380 is configured to focus and attract the magnetic beads onto a surface of the second electrochemical sensor 1325 once the magnetic beads are mixed with the biological sample.

Combined Immunoassay Methods

FIGS. 14-17 show exemplary flowcharts for performing the process steps of the present invention. The steps of FIGS. 14-17 may be implemented using the computing devices and systems described above with respect to FIGS. 1-13. Specifically, the flowcharts in FIGS. 14-17 illustrate the architecture, functionality, and operation of possible implementations of the systems, methods and computer program products according to several embodiments of the present invention. In this regard, each block in the flowcharts may represent a module, segment, or portion of code, which comprises one or more executable instructions stored on non-transitory machine readable storage medium that when executed by one or more processors (e.g., a processor of the analyzer) cause the one or more processors to perform the specified logical function(s) within the one or more executable instructions. It should also be noted that, in some alternative implementations, the functions noted in the blocks may occur out of the order noted in the figure. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts, or combinations of special purpose hardware and computer instructions.

Figure 14:
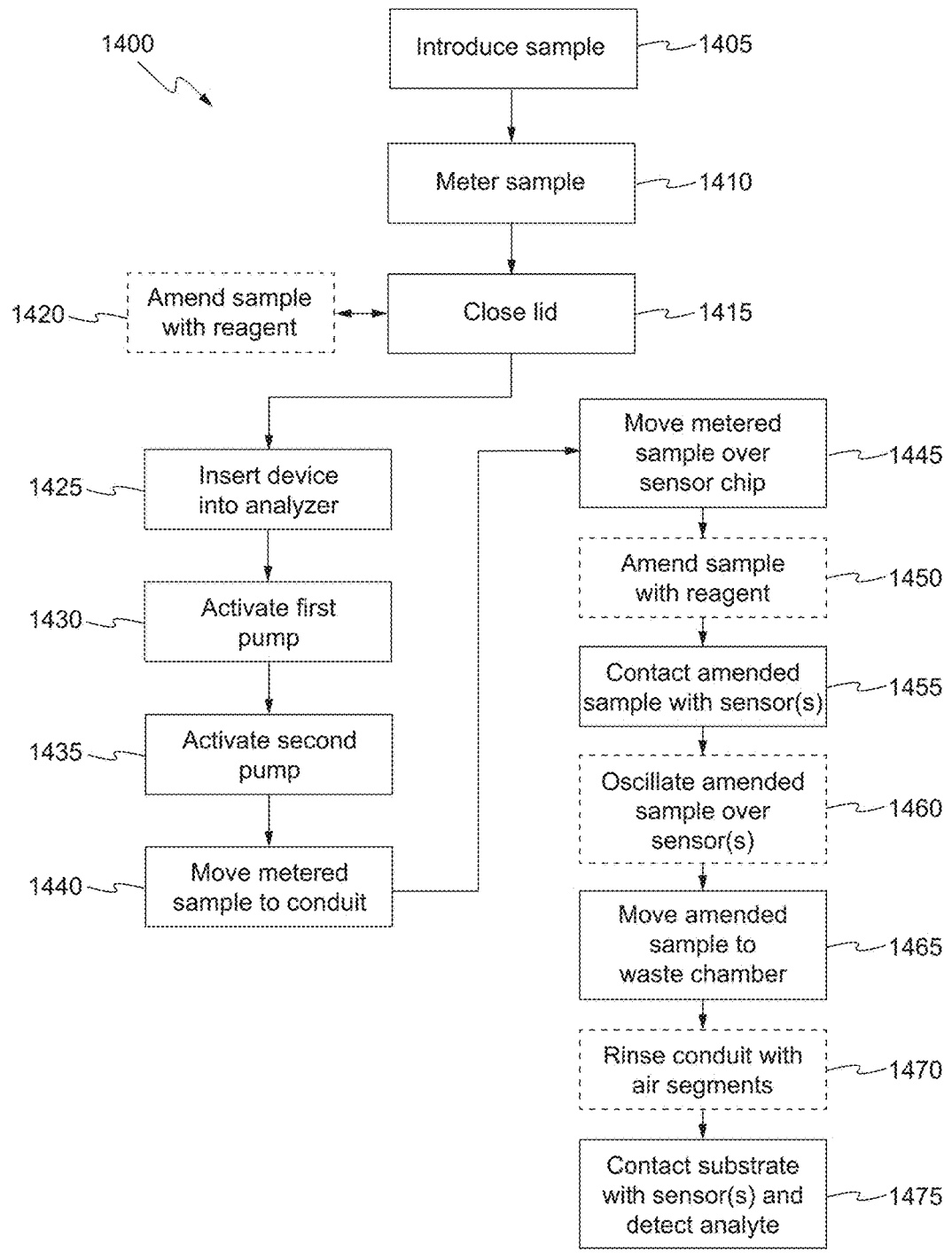
FIGS. 14-17 show processes in accordance with some aspects of the invention.

FIG. 14 illustrates a method 1400 (with reference to the sensing device 500 as illustrated in FIGS. 5A-5J) of using a sensing device in accordance with one embodiment of the invention. At step 1405, an unmetered biological sample may be introduced into a sample chamber (e.g., the sample chamber 510 described with respect to FIGS. 5G and 5H) of a sensing device, through a sample entry port (e.g., sealable sample entry port 506 described with respect to FIGS. 5B and 5C). At step 1410, a capillary stop (e.g., capillary stop 512 described with respect to FIGS. 5G and 5H) may prevent passage of the sample into a first conduit (e.g., conduit 531 described with respect to FIG. 5A) at this stage, and the sample chamber is filled with the sample. The capillary stop at the end of the sample chamber delimits a metered portion of the biological sample. At step 1415, a lid (e.g., closable sealing member 508 described with respect to FIGS. 5A and 5B) maybe closed to prevent leakage of the biological sample from out of the sensing device. While the biological sample is within sample chamber, the biological sample may be optionally amended at step 1420 with a compound or compounds (e.g., reagents such as antibody-coated magnetically susceptible beads and enzyme-labeled antibody conjugate) present initially as a dry coating on the inner surface of the chamber.

At step 1425, the sensing device may be inserted into an analyzer (e.g., analyzer 305 described with respect to FIG. 3) in accordance with some aspects of the present invention. At step 1430, insertion of the sensing device into the analyzer may activate a first pump (e.g., the portion of the flexible zone 536 as described with respect to FIGS. 5A and 5B) or mechanism that punctures a fluid-containing package when the package is pressed against a spike (e.g., spike 525 as described with respect to FIGS. 5G and 5H). Fluid (e.g., a substrate) may thereby expel into a second conduit (e.g., conduit 522 as described with respect to FIGS. 5G and 5H) that is in fluidic communication with the first conduit. A constriction in the second conduit prevents further movement of the fluid. At step 1435, operation of a second pump (e.g., displaceable membrane 526 as described with respect to FIGS. 5A, 5B, 5G, and 5H) by the analyzer applies pressure to an air-bladder of the sensing device, forcing air through a third conduit (e.g., conduit 529 as described with respect to FIGS. 5G and 5H) and into the sample chamber at a predetermined location.

At step 1440, the metered portion of the biological sample is expelled through the capillary stop by air pressure produced within the air-bladder at step 1435 into the first conduit. At step 1445, the biological sample is move forward within the first conduit to a portion of the first conduit (e.g., conduit 524 as described with respect to FIG. 5A) that is exposed to a sensor chip (e.g., sensor chip 604 as described with respect to FIG. 6B) by air pressure produced within the air-bladder. Optionally at step 1450, the biological sample is amended with a compound or compounds (e.g., reagents such as antibody-coated magnetically susceptible beads and enzyme-labeled antibody conjugate) present initially as a dry coating on a portion of the sensor chip (i.e., one or more reagent regions). To facilitate the dissolution of the compound or compounds in the biological sample and/or promote efficient sandwich formation on the magnetically susceptible beads, the biological sample may be oscillated over the one or more reagent regions by air pressure produced within the air-bladder. In one embodiment, an oscillation frequency of between about 0.2 Hz and about 5 Hz is used, most preferably about 0.7 Hz. At step 1455, the amended biological sample is move forward within the first conduit to a position over a first sensor (e.g., a low-end sensitivity amperometric sensor) and optionally a second sensor (e.g., a high-end sensitivity amperometric sensor) by air pressure produced within the air-bladder. Optionally at step 1460, to facilitate trapping the magnetically susceptible beads within a magnetic field on or near a surface of the second sensor and/or promote efficient sandwich formation on or near the surface of the first sensor comprising a biolayer, the biological sample may be oscillated over the first and second sensors by air pressure produced within the air-bladder. In one embodiment, an oscillation frequency of between about 0.2 Hz and about 5 Hz is used, most preferably about 0.7 Hz At step 1465, the biological sample is displaced from the first conduit by further pressure applied to air-bladder, and the biological sample passes to a waste chamber (e.g., waste chamber 516 as described with respect to FIGS. 5A and 5G.). At optional step 1470, one or more air segments (meniscus) may be produced within the first conduit by any suitable means, including a passive means, an embodiment of which is described in detail in U.S. Pat. No. 7,682,833, which is incorporated herein by reference in its entirety, or an active means including a transient lowering of the pressure within the first conduit using the second pump whereby air is drawn into the first conduit through a flap or valve. The one or more air segments are extremely effective at clearing or rinsing the biological sample-contaminated fluid from the first conduit. For example, a leading and/or trailing edge of the one or more air segments may be passed a number of times over the first and second sensors to rinse and resuspend extraneous material that may have been deposited from the biological sample. Extraneous material includes any material other than specifically bound analyte or analyte/antibody-enzyme conjugate complex. However, in accordance with various embodiments, the clearing or rinsing step 1470 using the one or more air segments is not sufficiently protracted or vigorous so as to promote substantial resuspension of the magnetically susceptible beads or dissociation of specifically bound analyte or analyte/antibody-enzyme conjugate complex from the beads or the biolayer.

At step 1475, the fluid in the second conduit is moved past the constriction into the first conduit and into contact with the first and second sensors by air pressure produced by the first pump. The fluid may include a substrate or signal agent and the enzyme remaining within the first conduit and immobilized on or near the first and second sensors either produces an electroactive species from an electroinactive substrate or destroys an electroactive substrate. In some embodiments, the fluid may be applied to the first immunosensor and the second immunosensor to wash the biological sample from the first second sensors. A change in current or potential generated by the production or destruction of the electroactive species at the first and second sensors, as appropriate to the mode of operation of the sensing device, is recorded as a function of time and determinative of the presence of a target analyte in the biological sample.

Figure 15:
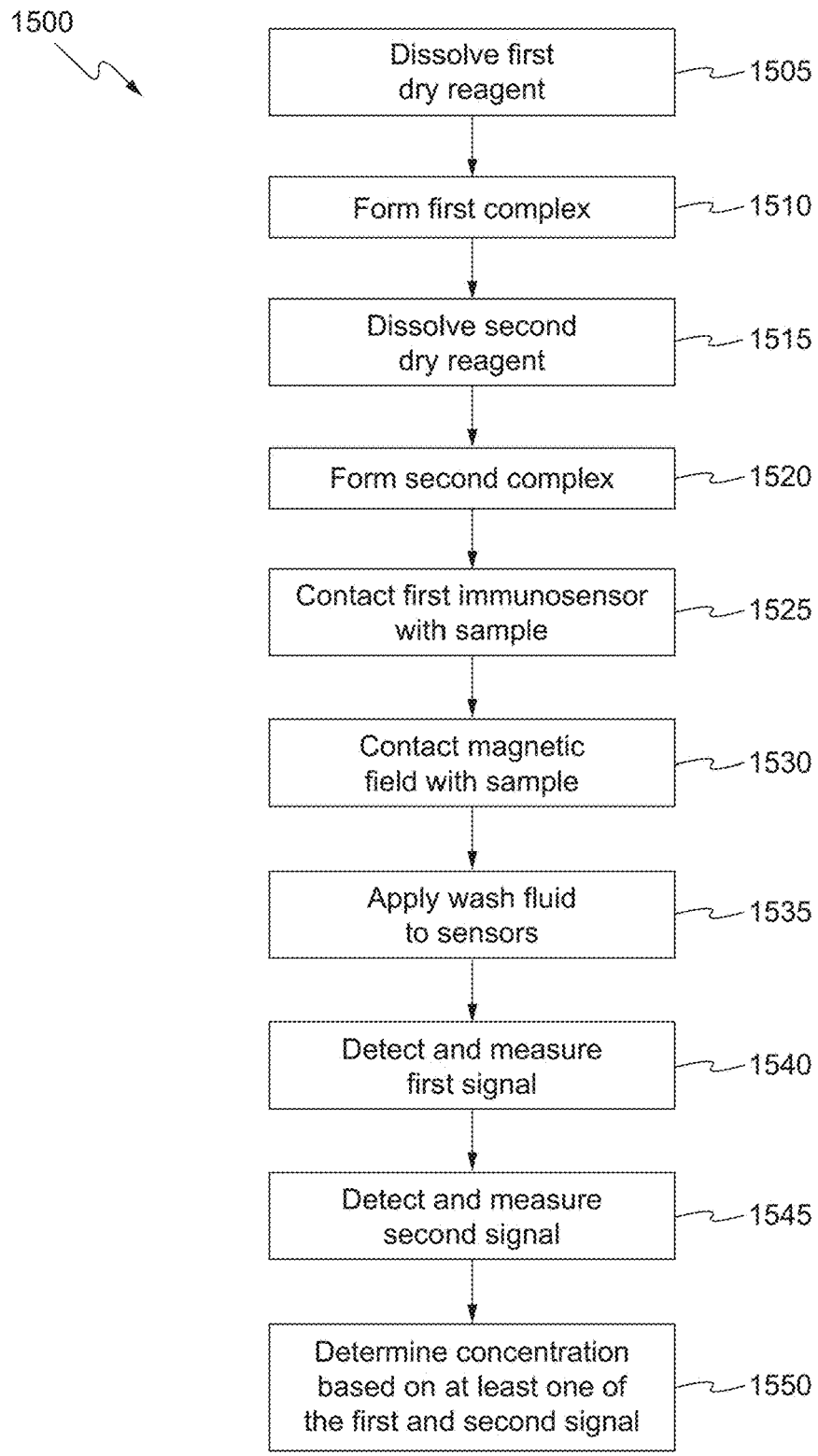

FIG. 15 illustrates a method 1500 of performing an immunoassay for determining the concentration of an analyte in a biological sample (e.g., whole blood) in accordance with one embodiment of the invention. At step 1505, a first dry reagent is dissolved into the biological sample. The first dry reagent may comprise an enzyme-biomolecule conjugate (e.g., signal antibodies) configured to bind to the analyte such as troponin I (TnI) or cardiac troponin I (cTnI). The enzyme-biomolecule conjugate includes an enzyme conjugated to biomolecules selected to bind to the analyte of interest. At step 1510, a first complex of the signal antibodies and the analyte is formed in a first liquid phase comprising the biological sample. At step 1515, a second dry reagent is dissolved into the biological sample. The second dry reagent may comprise magnetic beads or microspheres coated with capture biomolecules (e.g., capture antibodies immobilized on magnetic beads) configured to bind to the analyte. At step 1520, a second complex of the first complex (e.g., signal antibodies bound to the analyte) and the capture antibodies immobilized on the magnetic beads is formed in a second liquid phase comprising the biological sample.

At step 1525, the biological sample comprising the first complex and the second complex is contacted with a first immunosensor. The first immunosensor comprises a capture biomolecule (e.g., latex beads or microspheres coated with capture antibodies) immobilized on or near a surface of the first immunosensor. The capture antibodies are configured to bind to the analyte, to form a third complex localized on or near a solid phase boundary (e.g., a surface) of the first immunosensor. The third complex comprises the first complex (e.g., signal antibodies bound to the analyte) and the immobilized capture antibodies of the first immunosensor. The localization or capture of the analyte on or near a surface of the first immunosensor is the result of a heterogeneous reaction comprising the formation of the first complex in the first liquid phase and the formation of the third complex on or near the solid phase boundary. Thus, the first immunosensor may be recognized as a heterogeneous surface capture immunosensor.

At step 1530, the biological sample comprising the first complex and the second complex is contacted with a magnetic field localized around a second immunosensor. The magnetic field is configured to attract the magnetic beads in the biological sample such that the second complex of the first complex (e.g., signal antibodies bound to the analyte) and the capture antibodies immobilized on magnetic beads is localized on or near a surface of the second immunosensor. The localization or capture of the analyte on or near a surface of the second immunosensor is the result of a homogenous reaction comprising the formation of the first complex in the first liquid phase and the formation of the second complex on the second liquid phase. Thus, the second immunosensor may be recognized as a homogeneous magnetic bead capture immunosensor.

At step 1535, a fluid (e.g., a wash fluid) may be applied to the first immunosensor and the second immunosensor to wash the biological sample from the first immunosensor and the second immunosensor. The wash fluid may comprise a substrate or signal agent (e.g., phosphorylated molecule such as 4-aminophenylphosphate). At step 1540, a first signal is detected and measured at the first immunosensor from a reaction of the substrate with the third complex localized on or near the first immunosensor. For example a first electrochemical signal is detected and measured from the oxidation of an enzymatically produced electroactive species (e.g., 4-aminophenol) at a surface of the first immunosensor. The electroactive species is enzymatically produced from the reaction of the substrate with the enzyme-biomolecule conjugate in the third complex. In various embodiments, the substrate is a phosphorylated molecule (e.g., 4-aminophenylphosphate) configured such that when a phosphate moiety is removed by the enzyme-biomolecule conjugate (e.g., one or more antibodies bound to alkaline phosphatase), the molecule becomes electroactive. At step 1545, a second signal is detected and measured at the second immunosensor from a reaction of the substrate with the second complex localized on or near the second immunosensor. For example a second electrochemical signal is detected and measured from the oxidation of an enzymatically produced electroactive species (e.g., 4-aminophenol) at a surface of the second immunosensor. The electroactive species is enzymatically produced from the reaction of the substrate (e.g., 4-aminophenylphosphate) with the enzyme-biomolecule conjugate (e.g., one or more antibodies bound to alkaline phosphatase) in the second complex.

At step 1550, a concentration of the analyte in the biological sample is determined from at least one of the first signal and the second signal. In some embodiments, the first immunosensor is configured to generate the first signal as indicative of a concentration of the analyte in a first range (e.g., an upper concentration range that is greater than a lower concentration range) from a reaction of the substrate with the third complex, while the second immunosensor is configured to generate the second signal as indicative of a concentration of the analyte in a second range (e.g., a lower concentration range that is less than an upper concentration range) from a reaction of the substrate with the second complex.

In other embodiments in which the analyte is cardiac troponin, the first immunosensor is configured to generate the first signal as indicative of a concentration of the cardiac troponin concentration in a first range above about 1000 pg/mL from a reaction of the substrate with the third complex, while the second immunosensor is configured to generate the second signal as indicative of a concentration of the cardiac troponin concentration in a second range from about 0 to about 1000 pg/mL from a reaction of the substrate with the second complex (where about is +/−10 pg/ml around the endpoint of each range). As such, the first immunosensor determines the concentration of the cardiac troponin in a first range above about 1000 pg/mL based on the first signal, and the second immunosensor determines the concentration of the cardiac troponin in a second range from about 0 to about 1000 pg/mL based on the second signal. In alternative embodiments, the first range is above 2000 pg/mL, the second range is from 0 to 250 pg/ml, and the first signal and the second signal in combination (e.g., a weighted average) are indicative of the concentration of the cardiac troponin concentration in a range from 250 to 2000 pg/ml (where about is +/−10 pg/ml around the endpoint of each range). The average may be weighted based on one or more factors including the proximity of the calculated results to defined lower and upper crossover points, the ideality of the shape of the sensor current versus time plot, and the detection of an error condition at one of the sensors. As such, the first immunosensor determines the concentration of the cardiac troponin in a first range above about 2000 pg/mL based on the first signal, the second immunosensor determines the concentration of the cardiac troponin in a second range from about 0 to about 250 pg/mL based on the second signal, and a combination of the first immunosensor and the second immunosensor determines the concentration of the cardiac troponin in a third range from about 250 to about 2000 pg/mL based on the first signal and the second signal.

The lower concentration range (e.g., from about 0 to about 250 pg/mL) may be controlled by a time duration between dissolution of the magnetic beads into the sample and magnetic capture of the magnetic beads on or near the homogeneous magnetic bead capture immunosensor. In various embodiments, the time duration is between 1 and 20 minutes, preferably between 5 and 10 minutes. The lower concentration range may be further controlled by a dissolved concentration of the magnetic beads in the sample. In some embodiments, the dissolved concentration of the magnetic beads in the sample is in a range from about 10000 to 200000 beads per microliter, preferably between 10000 to 40000 beads per microliter. The lower concentration range may be further controlled by an affinity of each of the signal antibodies, an avidity of each of the signal antibodies, an affinity of each of the capture antibodies immobilized on the surface of the magnetic beads, and/or an avidity of each the capture antibodies immobilized on the surface of the magnetic beads. In some embodiments, the affinity of each of the signal antibodies is in a range from about $1\times10^7$ to about $1\times10^{13}$ M-1, preferably in a range from about $1\times10^{10}$ to about $1\times10^{13}$ M-1. In some embodiments, the avidity of each of the signal antibodies is in a range from about $1\times10^7$ to about $1\times10^{13}$ M-1, preferably in a range from about $1\times10^{10}$ to about $1\times10^{13}$ M-1. In some embodiments, the affinity of each of the capture antibodies immobilized on the surface of the magnetic beads is in a range from about $1\times10^7$ to about $1\times10^{13}$ M-1, preferably in a range from about $1\times10^{10}$ to about $1\times10^{13}$ M-1. In some embodiments, the avidity of each of the capture antibodies immobilized on the surface of the magnetic beads is in a range from about $1\times10^7$ to about $1\times10^{13}$ M-1, preferably in a range from about $1\times10^{10}$ to about $1\times10^{13}$ M-1. As should be understood, the lower concentration range (e.g., from about 0 to about 250 pg/mL) may be controlled by any number of the aforementioned factors alone or in combination, for example, the lower concentration range may be controlled by at least one of time duration between dissolution of the magnetic beads into the sample and magnetic capture of the magnetic beads on or near the homogeneous magnetic bead capture immunosensor, an affinity of each of the signal antibodies, an avidity of each of the signal antibodies, a dissolved concentration of the magnetic beads in the sample, an affinity of each of the capture antibodies immobilized on the surface of the magnetic beads, and an avidity of each the capture antibodies immobilized on the surface of the magnetic beads.

The upper concentration range (e.g., above about 2000 pg/mL) may be controlled by a time duration that the sample is positioned over the heterogeneous surface capture immunosensor. In various embodiments, the time duration is between 1 and 20 minutes, preferably between 5 and 10 minutes. The upper concentration range may be further controlled by an affinity of each of the signal antibodies, an avidity of each of the signal antibodies, an affinity of each of the capture antibodies immobilized on or near the heterogeneous surface capture immunosensor, and/or an avidity of each the capture antibodies immobilized on or near the heterogeneous surface capture immunosensor. In some embodiments, the affinity of each of the signal antibodies is in a range from about $1\times10^7$ to about $1\times10^{13}$ M-1, preferably in a range from about $1\times10^{10}$ to about $1\times10^{13}$ M-1. In some embodiments, the avidity of each of the signal antibodies is in a range from about $1\times10^7$ to about $1\times10^{13}$ M-1, preferably in a range from about $1\times10^{10}$ to about $1\times10^{13}$ M-1. In some embodiments, the affinity of each of the capture antibodies immobilized on or near the heterogeneous surface capture immunosensor is in a range from about $1\times10^7$ to about $1\times10^{13}$ M-1, preferably in a range from about $1\times10^{10}$ to about $1\times10^{13}$ M-1. In some embodiments, the avidity of each of the capture antibodies immobilized on or near the heterogeneous surface capture immunosensor is in a range from about $1\times10^7$ to about $1\times10^{13}$ M-1, preferably in a range from about $1\times10^{10}$ to about $1\times10^{13}$ M-1. As should be understood, the upper concentration range (e.g., above about 2000 pg/mL) may be controlled by any number of the aforementioned factors alone or in combination, for example, the upper concentration range may be controlled by at least one of time duration that the sample is positioned over the heterogeneous surface capture immunosensor, an affinity of each of the signal antibodies, an avidity of each of the signal antibodies, an affinity of each of the capture antibodies immobilized on or near the heterogeneous surface capture immunosensor, and an avidity of each the capture antibodies immobilized on or near the heterogeneous surface capture immunosensor.

Figure 16:
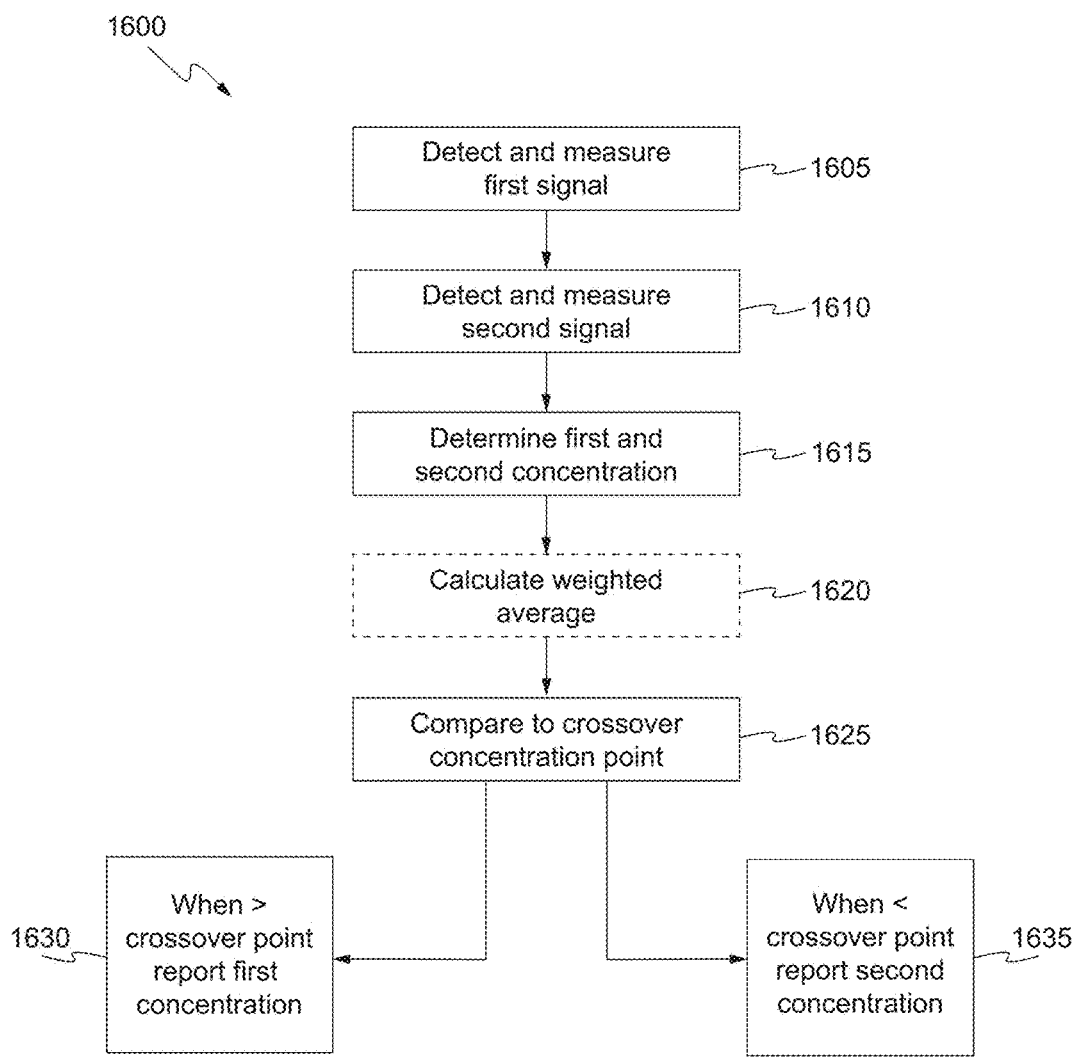

FIG. 16 illustrates a method 1600 for determining a concentration of an analyte in a sample over an extended concentration range in accordance with one embodiment of the invention. At step 1605, a first signal is detected and measured at a first immunosensor from a reaction of a substrate with a third complex localized on or near the first immunosensor in accordance with steps 1505-1540 of method 1500. At step 1610, a second signal is detected and measured at a second immunosensor from a reaction of a substrate with a second complex localized on or near the second immunosensor in accordance with steps 1505-1545 of method 1500. At step 1615, a first concentration of the analyte in the biological sample is determined from the first signal and a second concentration of the analyte in the biological sample is determined from the second signal. At optional step 1620, a weighted average of the first concentration and the second concentration is calculated. The average may be weighted based on one or more factors including the proximity of the calculated results to defined lower and upper crossover points, the ideality of the shape of the sensor current versus time plot, and the detection of an error condition at one of the sensors. At step, 1625, the first concentration and the second concentration, or optionally the weighted average are compared to a predetermined crossover concentration point. In various embodiments, the predetermined crossover concentration point is 1000 pg/ml, 1200 pg/ml, 1400 pg/ml, 1600 pg/ml, 1800 pg/ml, or 2000 pg/ml. At step 1630, when one or both of the first concentration and the second concentration, or optionally the weighted average are greater than the predetermined crossover concentration point, the first concentration of the analyte determined from the first signal is reported to a user of the device as the final concentration of the analyte in the biological sample. At step 1635, when one or both of the first concentration and the second concentration, or optionally the weighted average are less than the predetermined crossover concentration point, the second concentration of the analyte determined from the second signal is reported to a user of the device as the final concentration of the analyte in the biological sample.

Figure 17:
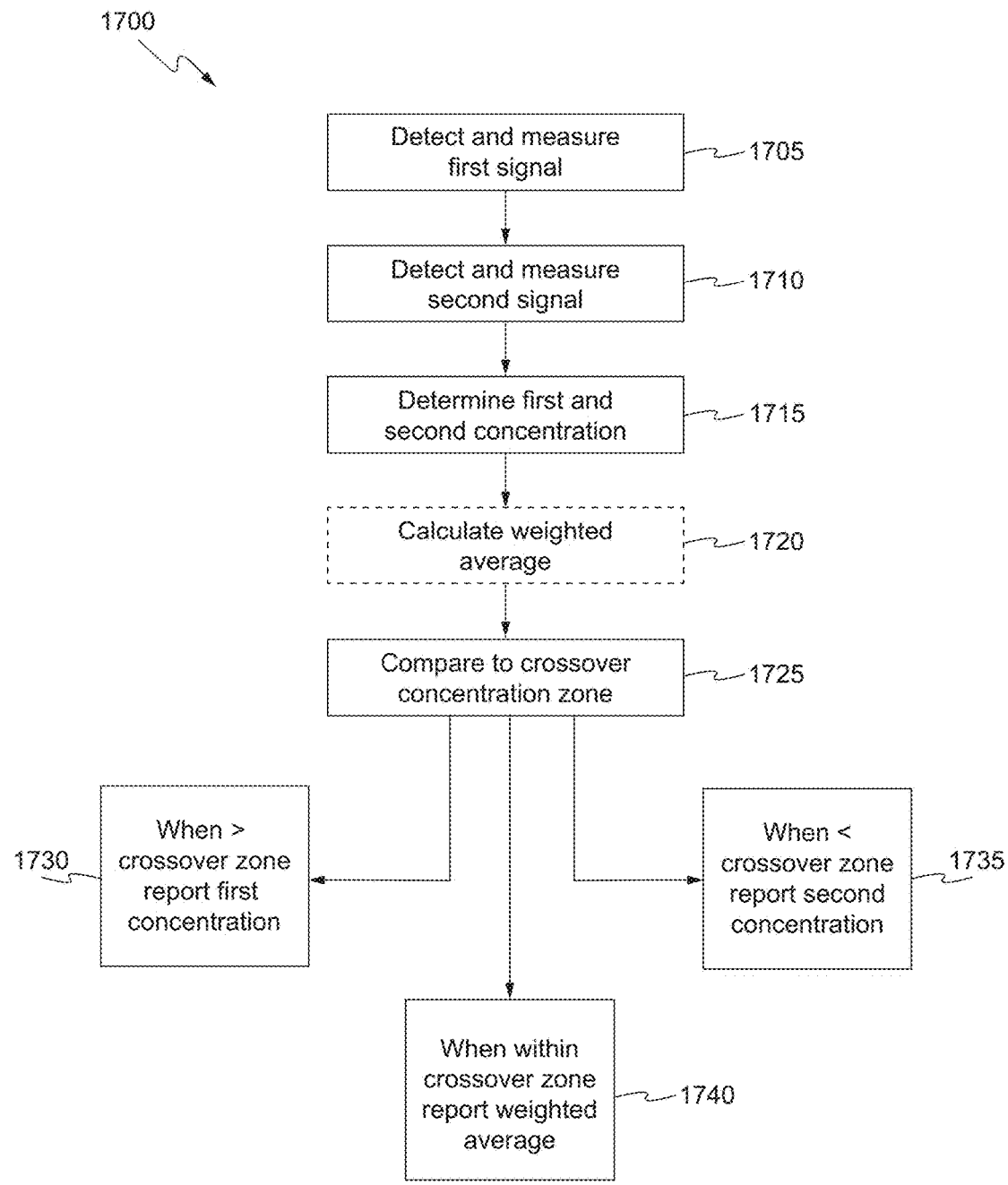

FIG. 17 illustrates a method 1700 for determining a concentration of an analyte in a sample over an extended concentration range in accordance with one embodiment of the invention. At step 1705, a first signal is detected and measured at a first immunosensor from a reaction of a substrate with a third complex localized on or near the first immunosensor in accordance with steps 1705-1745 of method 1700. At step 1710, a second signal is detected and measured at a second immunosensor from a reaction of a substrate with a second complex localized on or near the second immunosensor in accordance with steps 1705-1750 of method 1700. At step 1715, a first concentration of the analyte in the biological sample is determined from the first signal and a second concentration of the analyte in the biological sample is determined from the second signal. At optional step 1720, a weighted average of the first concentration and the second concentration is calculated. The average may be weighted based on one or more factors including the proximity of the calculated results to defined lower and upper crossover points, the ideality of the shape of the sensor current versus time plot, and the detection of an error condition at one of the sensors. At step, 1725, the first concentration and the second concentration, or optionally the weighted average are compared to a predetermined crossover concentration zone. In various embodiments, the predetermined crossover concentration zone is 400 to 2000 pg/ml, 600 to 1800 pg/ml, 400 to 1800 pg/ml, 800 to 1600 pg/ml, or 250 to 2000 pg/mL.

At step 1730, when one or both of the first concentration and the second concentration, or optionally the weighted average are greater than the predetermined crossover concentration zone, the first concentration of the analyte determined from the first signal is reported to a user of the device as the final concentration of the analyte in the biological sample. At step 1735, when one or both of the first concentration and the second concentration, or optionally the weighted average are less than the predetermined crossover concentration zone, the second concentration of the analyte determined from the second signal is reported to a user of the device as the final concentration of the analyte in the biological sample. At step 1740, when both of the first concentration and the second concentration, or optionally the weighted average are within the predetermined crossover concentration zone, the weighted average of the first concentration and the second concentration is reported to a user of the device as the final concentration of the analyte in the biological sample.

Figure 18:
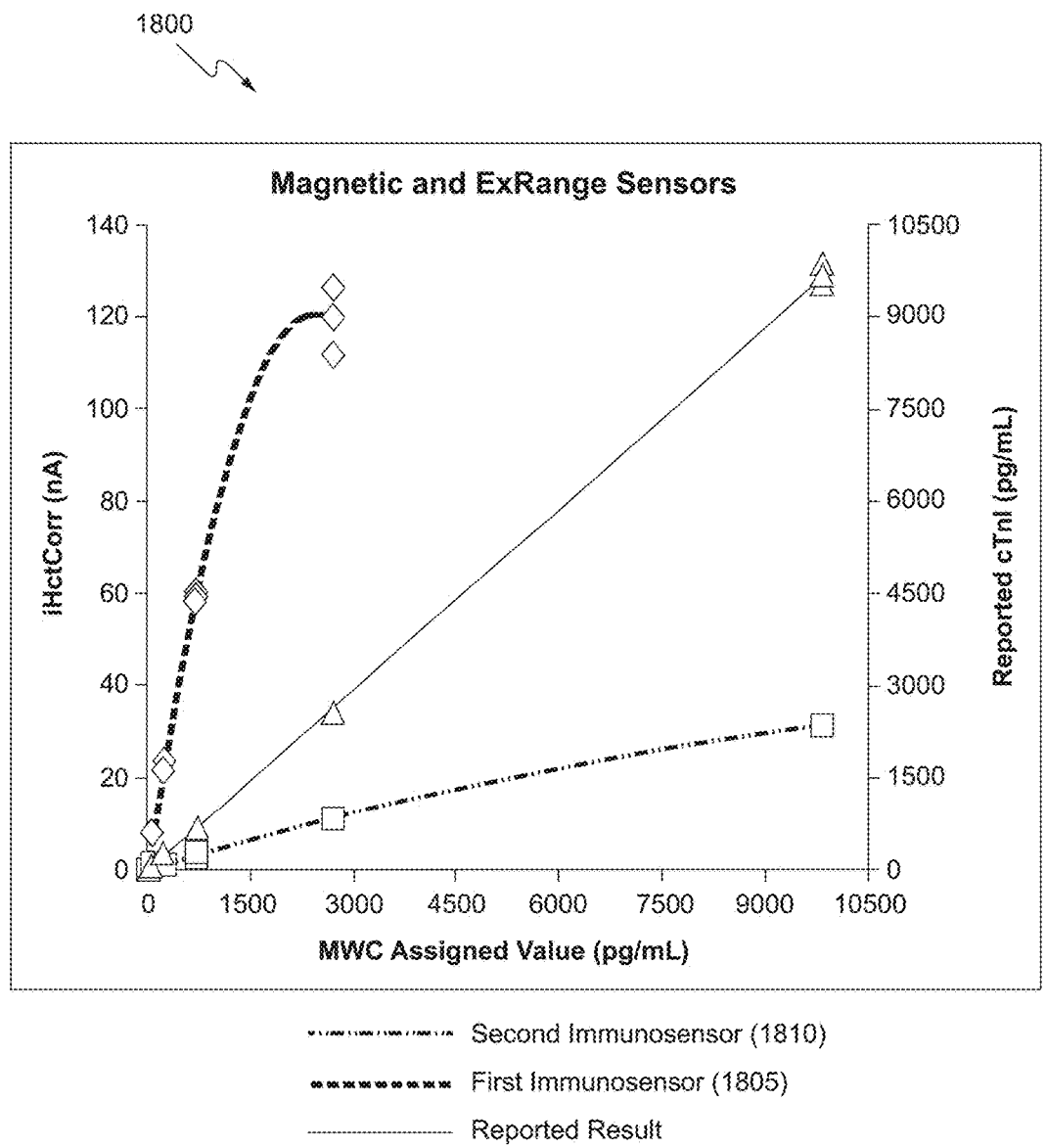
FIG. 18 shows a graph that illustrates the impact of being able to determine a concentration of an analyte in a sample over an extended concentration range in accordance with some aspects of the invention.

FIG. 18 shows a graph 1800 that illustrates the impact of being able to determine a concentration of an analyte in a sample over an extended concentration range in accordance with various embodiments of the invention. A microfabricated extended range sensor chip may include the first immunosensor 1805 (e.g., a low-end sensitivity amperometric sensor with an immobilized layer of capture antibodies) and the second immunosensor 1810 (e.g., a high-end sensitivity amperometric sensor with a magnetic field to attract magnetic beads with an immobilized layer of capture antibodies), as described herein. Graph 1800 shows that the first immunosensor 1805 is particularly well suited for detecting analytes having a higher concentration, for example, greater than 400 pg/ml, while the second immunosensor 1810 is particularly well suited for detecting analytes having a lower concentration, for example, less than 2000 pg/ml. Accordingly, by using a system having a sensor chip as described herein with both the first immunosensor 1805 (e.g., a low-end sensitivity amperometric sensor with an immobilized layer of capture antibodies) and the second immunosensor 1810 (e.g., a high-end sensitivity amperometric sensor with a magnetic field to attract magnetic beads with an immobilized layer of capture antibodies), it is possible to extend the range of concentrations that an analyte may be detected at by using the first and second signals generated at the respective immunosensors as described above with respect to methods 1500, 1600, and 1700.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A system for detecting cardiac troponin in a biological sample, the system comprising:
   one or more processors;
   a memory coupled to the one or more processors, the memory storing a plurality of instructions executable by the one or more processors, the plurality of instructions comprising instructions that when executed by the one or more processors cause the one or more processors to perform processing comprising:
   generating, by a first immunosensor, a first signal indicative of a first concentration of the cardiac troponin from a reaction of a signal agent with a first complex of capture antibodies immobilized on or near the first immunosensor, signal antibodies, and the cardiac troponin;
   generating, by a second immunosensor, a second signal indicative of a second concentration of the cardiac troponin from a reaction of the signal agent with a second complex of capture antibodies immobilized on magnetic beads localized on or near the second immunosensor sensor, the signal antibodies, and the cardiac troponin;
   determining the first concentration of the cardiac troponin in a first range above about 2000 pg/mL based on the first signal;
   determines determining the second concentration of the cardiac troponin in a second range from about 0 to about 250 pg/mL based on the second signal;
   determining a weighted average of the first concentration and the second concentration; and
   determining a third concentration of the cardiac troponin in a third range from about 250 to about 2000 pg/mL based on the weighted average.

2. The system of claim 1, wherein the cardiac troponin is cardiac troponin I (cTnI).

3. The system of claim 1, wherein the weighted average is determined based on one or more of the following factors: (i) a proximity of the first concentration and the second concentration to defined lower and upper crossover points, (ii) an ideality of a shape of a sensor current versus time plot, and (iii) a detection of an error condition at the first immunosensor or the second immunosensor.

4. The system of claim 1, wherein the first immunosensor and the second immunosensor are electrochemical immunosensors and the first signal and the second signal are electrochemical signals.

5. The system of claim 1, wherein the processing further comprises: moving, by a pump, the biological sample into contact with the first immunosensor and the second immunosensor, wherein a magnetic field is disposed locally around the second immunosensor, and wherein the moving the biological sample into contact with the second immunosensor facilitates attraction of the magnetic beads by the magnetic field and localization of the magnetic beads on or near the second immunosensor.

6. The system of claim 5, wherein the processing further comprises: moving, by the pump, the biological sample into contact with a first reagent region coated with the signal antibodies for the cardiac troponin.

7. The system of claim 6, wherein the processing further comprises: moving, by the pump, the biological sample into contact with second reagent region coated with the magnetic beads.

8. The system of claim 7, wherein the first reagent region, the second reagent region, the first immunosensor, and the second immunosensor are located on a substrate.

9. The system of claim 5, wherein the magnetic field is generated by a composite material including a binder and a particulate magnetic material.

10. The system of claim 9, wherein the binder is a polyimide or polyvinyl alcohol (PVA).

11. The system of claim 9, wherein the particulate magnetic material is comprised of neodymium iron boron (NdFeB) alloy or aluminum nickel cobalt (AlNiCo) alloy.

12. A method comprising:
    generating, by a first immunosensor, a first signal indicative of a first concentration of cardiac troponin in a biological sample from a reaction of a signal agent with a first complex of capture antibodies immobilized on or near the first immunosensor, signal antibodies, and the cardiac troponin;
    generating, by a second immunosensor, a second signal indicative of a second concentration of the cardiac troponin in the biological sample from a reaction of the signal agent with a second complex of capture antibodies immobilized on magnetic beads localized on or near the second immunosensor sensor, the signal antibodies, and the cardiac troponin;
    determining, by one or more processors, the first concentration of the cardiac troponin in a first range above about 2000 pg/mL based on the first signal;
    determining, by the one or more processors, the second concentration of the cardiac troponin in a second range from about 0 to about 250 pg/mL based on the second signal;
    determining, by the one or more processors, a weighted average of the first concentration and the second concentration; and
    determining, by the one or more processors, a third concentration of the cardiac troponin in a third range from about 250 to about 2000 pg/mL based on the weighted average.

13. A non-transitory computer-readable memory storing a plurality of instructions executable by one or more processors, the plurality of instructions comprising instructions that when executed by the one or more processors cause the one or more processors to perform processing comprising:
    generating, by a first immunosensor, a first signal indicative of a first concentration of cardiac troponin in a biological sample from a reaction of a signal agent with a first complex of capture antibodies immobilized on or near the first immunosensor, signal antibodies, and the cardiac troponin;
    generating, by a second immunosensor, a second signal indicative of a second concentration of the cardiac troponin in the biological sample from a reaction of the signal agent with a second complex of capture antibodies immobilized on magnetic beads localized on or near the second immunosensor sensor, the signal antibodies, and the cardiac troponin;

determining the first concentration of the cardiac troponin in a first range above about 2000 pg/mL based on the first signal;

determining the second concentration of the cardiac troponin in a second range from about 0 to about 250 pg/mL based on the second signal;

determining a weighted average of the first concentration and the second concentration; and determining a third concentration of the cardiac troponin in a third range from about 250 to about 2000 pg/mL based on the weighted average.

* * * * *